(12) United States Patent
Yarema et al.

(10) Patent No.: US 9,315,532 B2
(45) Date of Patent: Apr. 19, 2016

(54) FATTY ACID CARBOHYDRATE HYBRID MOLECULES AS THERAPEUTIC AGENTS AND METHODS THEREOF

(75) Inventors: Kevin J. Yarema, Woodstock, MD (US); Srinivasa-Gopalan Sampathkumar, Towson, MD (US); Mark B. Jones, Baltimore, MD (US); Christopher T. Campbell, Baltimore, MD (US); Udayanath Aich, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1672 days.

(21) Appl. No.: 11/920,909

(22) PCT Filed: May 24, 2006

(86) PCT No.: PCT/US2006/020389
§ 371 (c)(1),
(2), (4) Date: Jan. 15, 2009

(87) PCT Pub. No.: WO2006/127977
PCT Pub. Date: Nov. 30, 2006

(65) Prior Publication Data
US 2010/0144653 A1 Jun. 10, 2010

Related U.S. Application Data

(60) Provisional application No. 60/683,839, filed on May 24, 2005.

(51) Int. Cl.
C07H 5/04 (2006.01)
C07H 5/06 (2006.01)
C07H 1/00 (2006.01)

(52) U.S. Cl.
CPC .. *C07H 1/00* (2013.01); *C07H 5/04* (2013.01); *C07H 5/06* (2013.01)

(58) Field of Classification Search
None
See application file for complete search history.

(56) References Cited

U.S. PATENT DOCUMENTS 6,458,937 B1 * 10/2002 Bertozzi et al. ............. 536/1.11

FOREIGN PATENT DOCUMENTS

WO     WO01/87902     * 11/2001

OTHER PUBLICATIONS

Miyajima et al., Chem. Pharm. Bull., 44(12) 2268-2273, 1996.*
Byrn et al. Solid-State Chemistry of Drugs, 2d, Chapter 11 Hydrates and Solvates, 233-247, 2003.*
Morissette et al. Adv. Drug Delivery Rev. 2004, 56, 275-300.*
A.M. Rouhi, Chem. & Eng. News, Feb. 24, 2003, 81(8), 32-35.*
Inouye et al., Journal of the American Chemical Society, 1956, 78, pp. 4722-4724.*
Simerska et al., Journal of Molecular Catalysis B: Enzymatic, vol. 29, 2004, pp. 219-225.*
Kim et al.,Journal of Biological Chemistry, 2004, 279(18), 18342-18352.*
Wolfrom et al., J. Organic Chem., 32(6):1821-1823 (1967).

* cited by examiner

*Primary Examiner* — Traviss C McIntosh, III
(74) *Attorney, Agent, or Firm* — Mintz Levin Cohn Ferris Glovsky and Popeo, P.C.; Peter F. Corless; Richard B. Emmons

(57) ABSTRACT

Described herein are fatty acid carbohydrate hybrid compounds and derivatives thereof, and methods of treating or preventing disease and disease symptoms using the compounds and compositions thereof.

15 Claims, 9 Drawing Sheets a) Non specific diffusion across plasma membrane
b) Hydrolysis of butyrate by intracellular esterases But$_4$ManNAc (1)

But$_4$GlcNAc (2)

But$_5$Man (3)

Tributyrin (4)

Sodium butyrate (5)

R=CH$_3$CH$_2$CH$_2$CO-

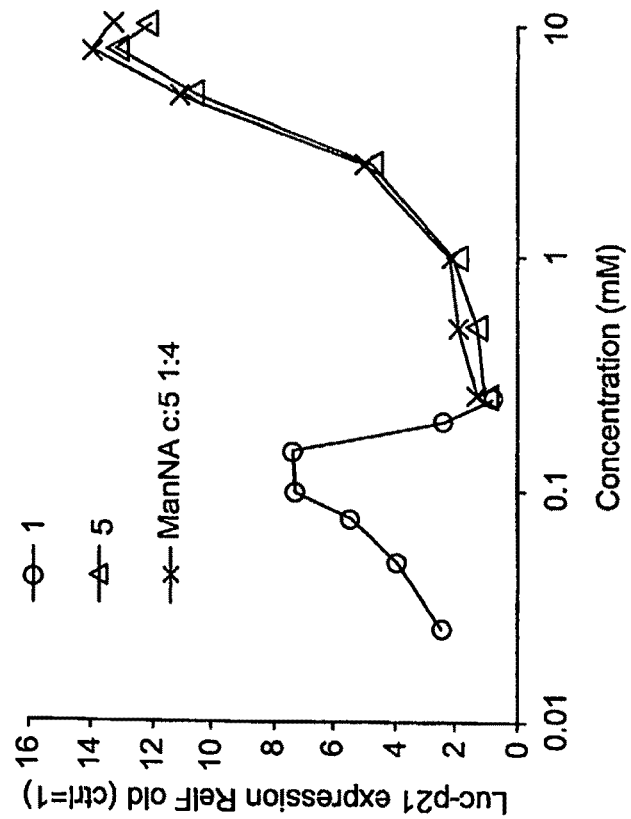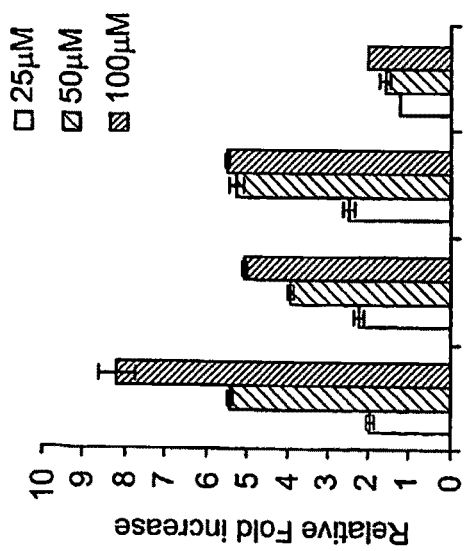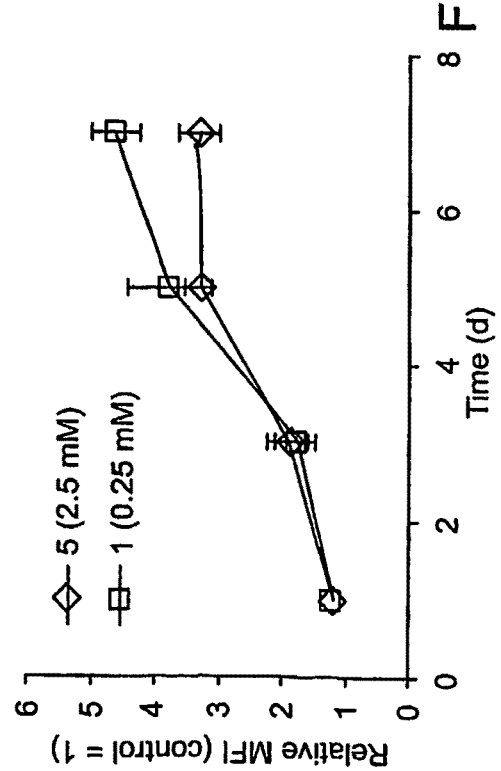
FIG. 4A
FIG. 4B
FIG. 4C

FATTY ACID CARBOHYDRATE HYBRID MOLECULES AS THERAPEUTIC AGENTS AND METHODS THEREOF

CROSS-REFERENCE TO RELATED APPLICATIONS

This application claims benefit of U.S. Application Ser. No. 60/683,839, filed May 24, 2005, which is incorporated by reference in its entirety.

STATEMENT REGARDING FEDERALLY SPONSORED RESEARCH OR DEVELOPMENT

Research supporting this application was carried out in part under funding from the National Institutes of Health (1R01CA112314-01A1), and the National Science Foundation (QSB-0425668). The government of the United States may have rights in the inventions.

BACKGROUND OF THE INVENTION

Described herein is the development of drugs that target two hallmarks of disease, including cancer, the loss of cell cycle checkpoint control (1) and abnormal glycosylation (2, 3). Uncontrolled cell proliferation characteristic of transformed cells is, at least in part, epigenetic in origin and results from cancer-specific anomalies in chromatin structure (4, 5). Chromatin consists of DNA, histones, and accessory proteins such as histone deacetylase (HDAC) and histone acetyltransferase (HAT). Together, HDAC and HAT remodel chromatin to provide a "code" that is recognized by the non-histone proteins that regulate gene expression (4). Not surprisingly, there is growing interest in the precise mechanisms that regulate chromatin remodeling with the bulk of these efforts focused on the inhibition of histone deacetylase (HDAC) activities. In recent years, the ability of HDAC inhibitors (HDACi) to disrupt the cell cycle or selectively induce apoptosis via de-repression of genes such as P21 and BAX in cancer cells, has made HDAC inhibition an attractive avenue for drug development (6) and intense efforts are underway to develop clinically-relevant HDACi for cancer therapy (7, 8).

In addition to epigenetic modifications, tumorigenesis frequently involves abnormal glycosylation that alters cell surface properties. These changes to the cell surface underlie altered cell adhesion and trigger abnormal inter- and intra-cellular signaling that simulate cell proliferation and metastasis. Examples of altered cell adhesion which contribute to metastasis include an initial decrease in adhesion that allows a malignant cell to break free of the primary tumor and a later increase in adhesion that allows a circulating cell to adhere to the vessel and extravasate into another tissue. Glycosylation, in particular sialylation, influence the changing adhesive properties of metastatic cells. Abnormal glycosylation also alters the interaction of cell-surface signaling molecules and produces abnormal inter- and intra-cellular signaling. For example, altered glycosylation of integrin influences its associations with other cell surface molecules. Therapies that disrupt the abnormal glycosylation of cancer cells might inhibit cell proliferation and metastasis.

n-Butyrate, a naturally-occurring HDACi belonging to the class of compounds known as short chain fatty acids (SCFAs) (9) has the attractive property of inducing cell cycle arrest and apoptosis in transformed cells while leaving healthy cells unharmed by reactivating cell cycle check point proteins such as p21$^{WAF1}$, a cyclin-dependent kinase inhibitor (10). Efforts to exploit n-butyrate for clinical treatment of cancer, however, have been stymied by its poor pharmacological properties and the high levels (up to 50 mM) needed for bioactivity (11). One approach to avoid the pharmacokinetic limitations of butyrate has been to use traditional enzyme-substrate screening assays to discover "drug-like" small molecule HDACi such as trichostatin (TSA), suberoyl hydroxamic acid (SAHA), and MS-275 among others (7). These compounds inhibit cell growth, induce terminal differentiation, and prevent tumor formation in animal models (12). Despite these attractive anti-cancer properties and nanomolar binding affinities to HDAC when tested against purified enzyme, the majority of current HDACi clinical candidates require unrealistically high (up to millimolar) concentrations to be effective against cells (4).

SUMMARY OF THE INVENTION

Described herein are compounds, and compositions and methods of generating the compounds thereof, methods of treating disease and disease symptoms, and compounds useful for modulating biological processes for treating disease and disease symptoms.

One embodiment is a compound of formula (I), (II) or (III), or pharmaceutically acceptable salt, solvate or hydrate thereof:

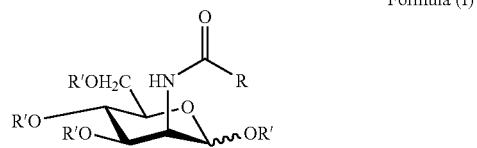

Formula (I)

wherein, each R' is independently H, —C(O)alkyl or —C(O)(CH$_2$)$_n$CH$_3$;

n is an integer 0-18; and each R is independently alkyl or alkenyl, each optionally substituted with 1-4 substituents selected from acyl, oxo, azido, aryl, halogen, —OC(O)alkyl, or —SC(O)alkyl;

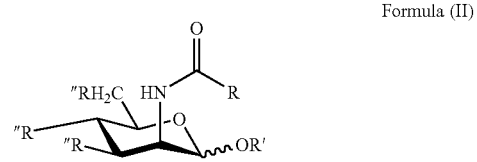

Formula (II)

wherein, each R' is independently is H, —C(O)alkyl or —C(O)(CH$_2$)$_n$CH$_3$;

each R" is independently is OH, OR', or F;

n is an integer 0-18; and each R is independently alkyl or alkenyl, each optionally substituted with 1-4 substituents selected from acyl, oxo, azido, aryl, halogen, —OC(O)alkyl, or —SC(O)alkyl;

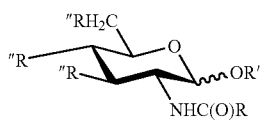

Formula (III)

wherein,
each R' is independently is H, —C(O)alkyl or —C(O)(CH$_2$)$_n$CH$_3$;
each R'' is independently is OH, OR', or F;
n is an integer 0-18; and
each R is independently alkyl or alkenyl, each optionally substituted with 1-4 substituents selected from acyl, oxo, azido, aryl, halogen, —OC(O)alkyl, or —SC(O)alkyl.

In other embodiments, the compounds are those of Formula (I), (II) or (III) or other formulae herein:
wherein n=any integer between 0-18, inclusive;
wherein n=any integer between a range X and Y, inclusive; where X is any integer between 0 and 17, inclusive, and Y is any integer between 1 and 18, inclusive;
wherein R is not C$_1$-C$_3$ alkyl substituted with —SC(O)CH$_3$;
wherein at least one R' is —C(O)alkyl;
wherein at least two R' are —C(O)alkyl;
wherein at least two R' are —C(O)alkyl and two R' are H.

Other aspects are the compounds of the formulae herein or pharmaceutically acceptable salt, solvate or hydrate thereof:
wherein each R' is independently C(O)CH$_3$; each R is independently: branched-chain alkyl, alkenyl, or C$_6$-C$_{10}$ straight chain alkyl, each optionally substituted with 1-4 substituents selected from acyl, azido, aryl, halogen, —OC(O)alkyl, or —SC(O)alkyl; or C$_1$-C$_5$ straight chain alkyl substituted with 1-4 substituents selected from aryl or halogen;
wherein R is —SC(O)alkyl;
wherein, each R' is independently C(O)CH$_3$; each R is independently alkyl or alkenyl, each optionally substituted with 1-4 substituents selected from acyl, azido, aryl, halogen, —OC(O)alkyl, or —SC(O)alkyl;
wherein R is not: (i) unsubstituted C$_1$-C$_5$ straight chain alkyl, (ii) C$_2$-C$_3$ alkyl substituted with acetyl, or (iii) C$_1$ alkyl substituted with azido or —OC(O)CH$_3$;
wherein each R' —C(O)(CH$_2$)$_n$CH$_3$ wherein n=0-4;
wherein at least one R' is —C(O)(CH$_2$)$_n$CH$_3$ wherein n=0-4;
wherein at least two R' are —C(O)(CH$_2$)$_n$CH$_3$ wherein n=0-4;
wherein at least three R' are —C(O)(CH$_2$)$_n$CH$_3$ wherein n=0-4;
wherein at least two R' are —C(O)(CH$_2$)$_n$CH$_3$ wherein n=0-4 and two R' are H.

Other aspect include:
A method of treating or preventing a subject (human, mammal, primate, rodent, mouse, rabbit, or other animal) suffering from or susceptible to a disease or disorder, the method comprising the step of administering to the subject a therapeutic amount of a compound herein sufficient to treat the disease or disorder or symptoms thereof under conditions such that the disease or disorder is treated;

A method of treating or preventing a subject suffering from or susceptible to a disease or disorder, the method comprising the steps of: (i) identifying the patient as in need of administration of a histone deacetylase inhibitor (HDACi) compound that activates sialic acid biosynthesis; and (ii) administering to the subject a therapeutic amount of a compound herein sufficient to treat or prevent the disease or disorder or symptoms thereof under conditions such that the disease or disorder is treated or prevented;

A method of inducing apoptosis in a subject, the method comprising the steps of identifying a subject as in need thereof and administering to the subject a therapeutic amount of a compound herein capable of inducing apoptosis;

A method of inducing apoptosis in a subject, the method comprising the steps of identifying a subject as in need thereof and administering to the subject a therapeutic amount of a compound of a compound herein capable of inducing apoptosis and activating silalic acid biosynthesis;

A method of sensitizing a cancer cell in a subject to anti-cancer agents, the method comprising the steps of identifying a subject as in need thereof and administering to the subject a therapeutic amount of a compound herein sufficient to sensitizing a cancer cell in a subject to anticancer agents;

A method of treating or preventing cancer in a subject, the method comprising the steps of administering to the subject a therapeutic amount of a compound herein, wherein the cancer is brain tumor, leukemia/lymphoma, colon cancer, breast cancer, lung cancer, prostate cancer, cervical cancer, bladder cancer, or thyroid cancer;

A method of modulating gene expression (e.g., p21WAF1/Cip1) in a subject, the method comprising the steps of identifying a subject as in need thereof and administering to the subject a therapeutic amount of a compound herein sufficient to modulate the protein (e.g., p21WAF1/Cip1);

A method of modulating sialyltransferase activity in a subject, the method comprising the steps of identifying a subject as in need thereof and administering to the subject a therapeutic amount of a compound herein sufficient to modulate the sialyltransferase activity;

A method of increasing the flux through the sialic acid biosynthetic pathway and increasing the biological production of sialic acid or its non-natural epitopes in sialic acid deficiency diseases (HIBM, stem cell development—genetic diseases) in a subject, the method comprising the steps of identifying a subject as in need thereof and administering to the subject a therapeutic amount of a compound herein sufficient to increasing the flux through the sialic acid biosynthetic pathway and increasing the biological production of sialic acid or its non-natural epitopes in sialic acid deficiency diseases;

A method herein wherein the modulation is up regulation;
A method herein wherein the modulation is down regulation;
A method herein wherein the modulation is increased production of sialic acid or its non-natural analogs;
A method by which to diagnose cytochemically or histochemically or histopathologically or immunocyto or immuno-histochemically, the modifications consequent to the expression of thiols on sialic acids; comprising the steps of assessing modulation of a target or process delineated herein;

A method of modulating a target, including a cell cycle checkpoint protein, programmed cell death substrate, or a kinase identified herein, in a cell comprising contacting a compound herein with a target (e.g., in a subject, in a cell, in vitro) such that the target is modulated.

Other aspects are the compounds delineated herein attached via a butyrate ester moiety to a biocompatible dendrimer or polymer (optionally on a a nanoscale) for uptake into a cell and release of butyrate (or other analog), including for targeted therapy (e.g., cystic fibrosis in the lung).

Other aspects include applications related to the compounds of the formulae herein used to treat neural or neurodegenerative or psychotic disorders. Other aspects include applications related to the compounds of the formulae herein (e.g., But$_4$GlcNAc) used as a control for ManNAc-sialic acid effects. The sugar GlcNAc is known to be pro-survival under stress conditions and But4GlcNAc has potential applications for enhanced delivery of GlcNAc—a C-2 epimer of ManNAc—along with concomitant effects on cell cycle arrest or tumor growth arrest.

The methods include administration of the compound or composition thereof to a subject in need (e.g., identified as in need) of such treatment.

Another aspect is a composition including a compound of any of the formulae herein and a pharmaceutically acceptable carrier. The composition can also include an additional therapeutic agent (e.g., anticancer agents). Additional anticancer agents include, for example, an antiangiogenesis agent, selective estrogen-receptor modulator (SERM), breast cancer therapeutic agent, aromatase inhibitor, biologic response modifiers, hormonal therapies agent, anthracycline, taxane, alkylating agent, taxol, cis-platin, arabinofuranosyl cytosine (ara-C), 5-fluorouracil (5-FU), altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPI-11, epothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, hydroxyurea, tamoxifen, raloxifene, toremifene, exemestane, letrozole, anastrozole, megestrol, trastuzumab, goserelin acetate, fulvestrant, doxorubicin, epirubicin, or cyclophosphonamide and the like.

One aspect is a method of treating a subject suffering from or susceptible to a disease or disorder, or symptom thereof, or preventing a disease or disorder, or symptom thereof, in a subject susceptible to a disease or disorder, or symptom thereof, or reducing the risk of development in a subject of a disease or disorder, or symptom thereof. The method includes the step of administering to the subject a therapeutic amount of a compound herein sufficient to treat the disease or disorder or symptom thereof under conditions such that the disease or disorder or symptom thereof is treated. In certain embodiments, the disease or disorder is a cancer or proliferative disease or disorder. In certain embodiments, the subject is a human. In certain embodiments, the subject is identified as being in need of such treatment. In certain embodiments, the subject is not suffering from a cancer. In certain embodiments, the subject is "at risk" of developing cancer. In certain embodiments, the method includes administration of an additional therapeutic agent. In certain embodiments, the step of administering comprises administering the compound orally, intravenously or intramuscularly.

In certain embodiments, the method further includes the step of determining a level of a marker in the subject. In certain embodiments, the step of determining of the level of Marker is performed prior to administration of the compound of the formulae hereinto the subject. In certain embodiments, the determining of the level of Marker is performed subsequent to administration of the compound of the formulae hereinto the subject. In certain embodiments, the determining of the level of Marker is performed prior to and subsequent to administration of the compound of the formulae hereinto the subject. In certain embodiments, the levels of Marker performed prior to and subsequent to administration of the compound of the formulae hereinto the subject are compared. In certain embodiments, the comparison of Marker levels is reported by a clinic, laboratory, or hospital agent to a health care professional. In certain embodiments, when the level of Marker performed prior to administration of the compound of the formulae hereinto the subject is lower or higher (depending on the Marker) than the level of Marker performed subsequent to administration of the compound of the formulae hereinto the subject, then the amount of compound administered to the subject is an effective amount. The Marker can be any characteristic or identifier, including for example, a chemical, a fluid, a protein, gene, promoter, enzyme, protein, labeled molecule, tagged molecule, antibody, and the like (e.g., HDAC, p21, glycosylation, BAX, sialyltransferase, sialidase, phosphorylation of a kinase, polysialic acid, sialyl Lewis X, gangliosides, chemical epitopes such as thiols, ketones and azides; the expression of genes, including the following, —MUC1, MUC18, galectin 3, galectin 12, galectin-related inhibitor of proliferation isoform b, chondroitin 6-sulfo T, MUC1—transmembrane, COG7, interferon induced transmembrane protein 1 (9-27), anaphase promoting complex subunit 5 (ANAPCS), sperm associated antigen 7 (SPAG7), proteasome activator subunit 1 (pA28 alpha), heparanase, melanoma cell adhesion molecule (short transcript), serglycin, syndecan 4 (ryudocan), ppGalNAc T11, xylosyltransferase II 9XT-II) [GAG enzyme], similar to glucosamine-phosphate N-acetyltransferase (short), gp130-RAPS, erythropoietin receptor, insulin-like GF 2 receptor, insulin-like GF 3, TGF, beta receptor III and follistatin isoform FST317 precursor.

Another aspect is a method of inducing apoptosis in a cell (e.g., cancerous cell) in a subject, the method comprising the steps of identifying a subject as in need thereof and administering to the subject a therapeutic amount of a compound of the formulae herein sufficient to induce apoptosis in a cell.

Another aspect is a method of impairing abnormal remodeling of the extracellular matrix by diseased or injured cells (fibroblasts) in a subject, the method comprising the steps of identifying a subject as in need thereof and administering to the subject a therapeutic amount of a compound of the formulae herein sufficient to impair abnormal remodeling of the extracellular matrix by diseased or injured cells. Such method is relevant as a method to treat myocardial infarction, osteoid and rheumatoid arthritis, and fibrosis.

Another aspect is a method of impairing invasiveness and motility of abnormal cells that infiltrate diseased tissue (e.g., cancer cells or autoreactive immune cells) in a subject, the method comprising the steps of identifying a subject as in need thereof and administering to the subject a therapeutic amount of a compound of the formulae herein sufficient to impair invasiveness and motility of abnormal cells that infiltrate diseased tissue. Such method is relevant as a method to treat or prevent metastatic cancer, rheumatoid arthritis, Crohn's disease, and multiple sclerosis.

Another aspect is a method of treating or preventing multiple sclerosis, Crohn's disease, rheumatoid arthritis, fibrosis, myocardial infarction, osteoid arthritis, Kaposi's sarcoma-associated herpes virus, Parkinson's disease, Hungtington's disease, spinal muscular atrophy (increase survival motor neuron protein), cystic fibrosis, ulcerative colitis, antibiotic-associated diarrhea, stem cell fate and regenerative medicine, immune disorders, congenital abnormalities, infectious diseases and related diseases in a subject, the method comprising the steps of identifying a subject as in need thereof and administering to the subject a therapeutic amount of a compound of the formulae herein sufficient to treat or prevent multiple sclerosis, Crohn's disease, rheumatoid arthritis, fibrosis, myocardial infarction, osteoid arthritis, Kaposi's sarcoma-associated herpes virus, Parkinson's disease, Hungtington's disease, spinal muscular atrophy (increase survival motor neuron protein), cystic fibrosis, ulcerative colitis, antibiotic-associated diarrhea, stem cell fate and regenerative medicine, immune disorders, congenital abnormalities, infectious diseases and related diseases.

Another aspect is a method of sensitizing a cancer cell in a subject to an anticancer agent or DNA targeted agent (e.g., chemotherapeutic), the method comprising the steps of identifying a subject as in need thereof and administering to the subject a therapeutic amount of a compound of the formulae herein sufficient to sensitizing a cancer cell in a subject to an anticancer agent or DNA targeted agent.

Another aspect is a method of treating or preventing cancer in a subject, the method comprising the steps of and administering to the subject a therapeutic amount of a compound of the formulae herein. In another aspect, the method further comprises administration of an additional anticancer agent. In another aspect, the additional anticancer agent is a DNA targeted agent (e.g., chemotherapeutic). In another aspect, the method further comprises administration of ionizing radiation. In other aspects, the cancer is colon, lung, breast, bladder, melanoma, prostate or other solid malignancies or blood related cancers such as leukemia and lymphoma.

Another aspect is a method of modulating a protein or gene capable of expressing such protein (e.g., HDAC, p21, BAX, MMPs (matrix metalloproteinases), NF-κB, AP-1, β-catenin, phosphatidyl serine, MUC1, MUC18, galectin 3, galectin 12, galectin-related inhibitor of proliferation isoform b, chondroitin 6-sulfo T, MUC1-transmembrane, COG7, interferon induced transmembrane protein 1 (9-27), anaphase promoting complex subunit 5 (ANAPC5), sperm associated antigen 7 (SPAG7), proteasome activator subunit 1 (pA28 alpha), heparanase, melanoma cell adhesion molecule (short transcript), serglycin, syndecan 4 (ryudocan), ppGalNAc T11, xylosyltransferase II 9XT-II) [GAG enzyme], similar to glucosamine-phosphate N-acetyltransferase (short), gp130-RAPS, erythropoietin receptor, insulin-like GF 2 receptor, insulin-like GF 3, TGF, beta receptor III and follistatin isoform FST317 precursor.) in a subject, the method comprising the steps of identifying a subject as in need thereof and administering to the subject a therapeutic amount of a compound of the formulae herein sufficient to modulate the protein or gene capable of expressing such protein (e.g., HDAC, p21, BAX, MMPs (matrix metalloproteinases), NF-κB, AP-1, β-catenin, phosphatidyl serine, MUC1, MUC18, galectin 3, galectin 12, galectin-related inhibitor of proliferation isoform b, chondroitin 6-sulfo T, MUC1-transmembrane, COG7, interferon induced transmembrane protein 1 (9-27), anaphase promoting complex subunit 5 (ANAPC5), sperm associated antigen 7 (SPAG7), proteasome activator subunit 1 (pA28 alpha), heparanase, melanoma cell adhesion molecule (short transcript), serglycin, syndecan 4 (ryudocan), ppGalNAc T11, xylosyltransferase II 9XT-II) [GAG enzyme], similar to glucosamine-phosphate N-acetyltransferase (short), gp130-RAPS, erythropoietin receptor, insulin-like GF 2 receptor, insulin-like GF 3, TGF, beta receptor III and follistatin isoform FST317 precursor.).

Another aspect is a method to extend the lifetime of a subject who is refractory to current anti-cancer chemotherapy and to improve the quality of life for those subjects. Such method includes the steps of identifying a subject as in need thereof and administering to the subject a therapeutic amount of a compound of the formulae herein sufficient to prevent, reduce or ameliorate metastasis of cancer.

Another aspect is a method of modulating HDAC and/or glycosylation in a subject, the method comprising the steps of identifying a subject as in need thereof and administering to the subject a therapeutic amount of a compound of any of the formulae herein sufficient to modulate HDAC and/or glycosylation under conditions such that the HDAC and/or glycosylation is modulated. In one aspect, the modulation is down regulation of HDAC. In another aspect, the modulation is up regulation of biosynthesis of sialic acids.

A method of treating or preventing a subject suffering from or susceptible to a disease or disorder, the method comprising the steps of: (i) identifying the patient as one who may benefit from cell cycle inhibition (e.g., HDAC inhibition) and/or abnormal glycosylation modulation (e.g., sialic acid biosynthesis); and (ii) administering to the subject a therapeutic amount of a compound of the formulae herein sufficient to treat or prevent the disease or disorder or symptoms thereof under conditions such that the disease or disorder is treated or prevented or prevented from further progression.

In another aspect, an embodiment provides kits for treatment of a disease(s) or disorder(s) or symptoms thereof, including those of a proliferative disorder nature. In one embodiment, the kit includes an effective amount of a compound of the formulae herein in unit dosage form, together with instructions for administering the compound of the formulae hereinto a subject suffering from or susceptible to a disease or disorder or symptoms thereof, including those of a proliferative disorder nature and metastatic cancer. In preferred embodiments, the compound of the formulae herein is any of the specific compounds delineated herein.

Another aspect is a method of modulating a target, including a cell cycle checkpoint protein, programmed cell death substrate, or a kinase identified herein, in a cell comprising contacting a compound of any of the formulae herein with a target (e.g., in a subject, in a cell, in vitro) such that the target is modulated. The method can also include modulating the target in a subject by administering the compound to the subject.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Another aspect is a method of making a pharmaceutical composition delineated herein, including the step of combining a compound herein (e.g., a compound of any of the formulae herein) with a pharmaceutically acceptable carrier. The method can further include combining an additional therapeutic agent with the compound and/or carrier.

Table A lists compounds (or salts or solvates thereof) that are representative embodiments of the formulae herein and are useful in the methods delineated herein.

TABLE A

Compounds Combinatorial Approach for the synthesis of bifunctional prodrugs containing short chain fatty acids (SCFA) and non-natural ManNAc analogs as potential therapeutic agents for cancer and regenerative medicine, using 2 as a scaffold.

Reaction scheme: Compound 1 (R'OH$_2$C, NH$_3{}^+$Ox$^-$, R'O, R'O, OR'; R' = H, acyl, alkyl) + RCO$_2$H, EDC, triethylamine, RT, DMF → Compound 2 (R'OH$_2$C, HN-C(=O)-R, R'O, R'O, OR')

| Compound No. | R' | R |
|---|---|---|
| 1 | H | —CH$_3$ |
| 2 | H | —(CH$_2$)$_n$CH$_3$; n = 1 |
| 3 | H | —(CH$_2$)$_n$CH$_3$; n = 2 |
| 4 | H | —(CH$_2$)$_n$CH$_3$; n = 3 |
| 5 | H | —(CH$_2$)$_n$CH$_3$; n = 4 |
| 6 | H | —(CH$_2$)$_n$CH$_3$; n = 5 |
| 7 | H | —(CH$_2$)$_n$CH$_3$; n = 6 |
| 8 | H | —CH$_2$(CH$_2$)$_n$COCH$_3$; n = 1 |
| 9 | H | —CH$_2$(CH$_2$)$_n$COCH$_2$CH$_3$; n = 1 |
| 10 | H | —CH$_2$(CH$_2$)$_n$COCH$_3$; n = 2 |
| 11 | H | —CH$_2$(CH$_2$)$_n$COCH$_3$; n = 3 |
| 12 | H | —CH$_2$(CH$_2$)$_n$COCH$_3$; n = 4 |
| 13 | H | —CH$_2$N$_3$ |
| 14 | H | —CH$_2$OCOCH$_3$ |
| 15 | H | —(CH$_2$)$_n$SCOCH$_3$; n = 1 |
| 16 | H | —(CH$_2$)$_n$SCOCH$_3$; n = 2 |
| 17 | H | —(CH$_2$)$_n$SCOCH$_3$; n = 3 |
| 18 | H | —CH$_2$Ph |
| 19 | H | —CH(CH$_3$)$_2$ |
| 20 | H | —CH$_2$CF$_3$ |
| 21 | H | —(CH$_2$)$_3$CH(CH$_3$)$_2$ |
| 22 | H | —CH$_2$C=CH(CH$_3$) |
| 23 | COCH$_3$ | —CH$_3$ |
| 24 | COCH$_3$ | —(CH$_2$)$_n$CH$_3$; n = 1 |
| 25 | COCH$_3$ | —(CH$_2$)$_n$CH$_3$; n = 2 |
| 26 | COCH$_3$ | —(CH$_2$)$_n$CH$_3$; n = 3 |
| 27 | COCH$_3$ | —(CH$_2$)$_n$CH$_3$; n = 4 |
| 28 | COCH$_3$ | —(CH$_2$)$_n$CH$_3$; n = 5 |
| 29 | COCH$_3$ | —(CH$_2$)$_n$CH$_3$; n = 6 |
| 30 | COCH$_3$ | —CH$_2$(CH$_2$)$_n$COCH$_3$; n = 1 |
| 31 | COCH$_3$ | —CH$_2$(CH$_2$)$_n$COCH$_2$CH$_3$; n = 1 |
| 32 | COCH$_3$ | —CH$_2$(CH$_2$)$_n$COCH$_3$; n = 2 |
| 33 | COCH$_3$ | —CH$_2$(CH$_2$)$_n$COCH$_3$; n = 3 |
| 34 | COCH$_3$ | —CH$_2$(CH$_2$)$_n$COCH$_3$; n = 4 |
| 35 | COCH$_3$ | —CH$_2$N$_3$ |
| 36 | COCH$_3$ | —CH$_2$OCOCH$_3$ |
| 37 | COCH$_3$ | —(CH$_2$)$_n$SCOCH$_3$; n = 1 |
| 38 | COCH$_3$ | —(CH$_2$)$_n$SCOCH$_3$; n = 2 |
| 39 | COCH$_3$ | —(CH$_2$)$_n$SCOCH$_3$; n = 3 |
| 40 | COCH$_3$ | —CH$_2$Ph |
| 41 | COCH$_3$ | —CH(CH$_3$)$_2$ |
| 42 | COCH$_3$ | —CH$_2$CF$_3$ |
| 43 | COCH$_3$ | —(CH$_2$)$_3$CH(CH$_3$)$_2$ |
| 44 | COCH$_3$ | —CH$_2$C=CH(CH$_3$) |
| 45 | COCH$_2$CH$_3$ | —CH$_3$ |
| 46 | COCH$_2$CH$_3$ | —(CH$_2$)$_n$CH$_3$; n = 1 |
| 47 | COCH$_2$CH$_3$ | —(CH$_2$)$_n$CH$_3$; n = 2 |
| 48 | COCH$_2$CH$_3$ | —(CH$_2$)$_n$CH$_3$; n = 3 |
| 49 | COCH$_2$CH$_3$ | —(CH$_2$)$_n$CH$_3$; n = 4 |
| 50 | COCH$_2$CH$_3$ | —(CH$_2$)$_n$CH$_3$; n = 5 |
| 51 | COCH$_2$CH$_3$ | —(CH$_2$)$_n$CH$_3$; n = 6 |
| 52 | COCH$_2$CH$_3$ | —CH$_2$(CH$_2$)$_n$COCH$_3$; n = 1 |
| 53 | COCH$_2$CH$_3$ | —CH$_2$(CH$_2$)$_n$COCH$_2$CH$_3$; n = 1 |
| 54 | COCH$_2$CH$_3$ | —CH$_2$(CH$_2$)$_n$COCH$_3$; n = 2 |
| 55 | COCH$_2$CH$_3$ | —CH$_2$(CH$_2$)$_n$COCH$_3$; n = 3 |
| 56 | COCH$_2$CH$_3$ | —CH$_2$(CH$_2$)$_n$COCH$_3$; n = 4 |
| 57 | COCH$_2$CH$_3$ | —CH$_2$N$_3$ |
| 58 | COCH$_2$CH$_3$ | —CH$_2$OCOCH$_3$ |
| 59 | COCH$_2$CH$_3$ | —(CH$_2$)$_n$SCOCH$_3$; n = 1 |
| 60 | COCH$_2$CH$_3$ | —(CH$_2$)$_n$SCOCH$_3$; n = 2 |
| 61 | COCH$_2$CH$_3$ | —(CH$_2$)$_n$SCOCH$_3$; n = 3 |
| 62 | COCH$_2$CH$_3$ | —CH$_2$Ph |
| 63 | COCH$_2$CH$_3$ | —CH(CH$_3$)$_2$ |
| 64 | COCH$_2$CH$_3$ | —CH$_2$CF$_3$ |
| 65 | COCH$_2$CH$_3$ | —(CH$_2$)$_3$CH(CH$_3$)$_2$ |
| 66 | COCH$_2$CH$_3$ | —CH$_2$C=CH(CH$_3$) |
| 67 | CO(CH$_2$)$_n$CH$_3$; n = 2 | —CH$_3$ |
| 68 | CO(CH$_2$)$_n$CH$_3$; n = 2 | —(CH$_2$)$_n$CH$_3$; n = 1 |
| 69 | CO(CH$_2$)$_n$CH$_3$; n = 2 | —(CH$_2$)$_n$CH$_3$; n = 2 |
| 70 | CO(CH$_2$)$_n$CH$_3$; n = 2 | —(CH$_2$)$_n$CH$_3$; n = 3 |
| 71 | CO(CH$_2$)$_n$CH$_3$; n = 2 | —(CH$_2$)$_n$CH$_3$; n = 4 |
| 72 | CO(CH$_2$)$_n$CH$_3$; n = 2 | —(CH$_2$)$_n$CH$_3$; n = 5 |
| 73 | CO(CH$_2$)$_n$CH$_3$; n = 2 | —(CH$_2$)$_n$CH$_3$; n = 6 |
| 74 | CO(CH$_2$)$_n$CH$_3$; n = 2 | —CH$_2$(CH$_2$)$_n$COCH$_3$; n = 1 |
| 75 | CO(CH$_2$)$_n$CH$_3$; n = 2 | —CH$_2$(CH$_2$)$_n$COCH$_2$CH$_3$; n = 1 |
| 76 | CO(CH$_2$)$_n$CH$_3$; n = 2 | —CH$_2$(CH$_2$)$_n$COCH$_3$; n = 2 |
| 77 | CO(CH$_2$)$_n$CH$_3$; n = 2 | —CH$_2$(CH$_2$)$_n$COCH$_3$; n = 3 |
| 78 | CO(CH$_2$)$_n$CH$_3$; n = 2 | —CH$_2$(CH$_2$)$_n$COCH$_3$; n = 4 |
| 79 | CO(CH$_2$)$_n$CH$_3$; n = 2 | —CH$_2$N$_3$ |
| 80 | CO(CH$_2$)$_n$CH$_3$; n = 2 | —CH$_2$OCOCH$_3$ |
| 81 | CO(CH$_2$)$_n$CH$_3$; n = 2 | —(CH$_2$)$_n$SCOCH$_3$; n = 1 |
| 82 | CO(CH$_2$)$_n$CH$_3$; n = 2 | —(CH$_2$)$_n$SCOCH$_3$; n = 2 |
| 83 | CO(CH$_2$)$_n$CH$_3$; n = 2 | —(CH$_2$)$_n$SCOCH$_3$; n = 3 |
| 84 | CO(CH$_2$)$_n$CH$_3$; n = 2 | —CH$_2$Ph |
| 85 | CO(CH$_2$)$_n$CH$_3$; n = 2 | —CH(CH$_3$)$_2$ |
| 86 | CO(CH$_2$)$_n$CH$_3$; n = 2 | —CH$_2$CF$_3$ |
| 87 | CO(CH$_2$)$_n$CH$_3$; n = 2 | —(CH$_2$)$_3$CH(CH$_3$)$_2$ |
| 88 | CO(CH$_2$)$_n$CH$_3$; n = 2 | —CH$_2$C=CH(CH$_3$) |
| 89 | CO(CH$_2$)$_n$CH$_3$; n = 3 | —CH$_3$ |
| 90 | CO(CH$_2$)$_n$CH$_3$; n = 3 | —(CH$_2$)$_n$CH$_3$; n = 1 |
| 91 | CO(CH$_2$)$_n$CH$_3$; n = 3 | —(CH$_2$)$_n$CH$_3$; n = 2 |
| 92 | CO(CH$_2$)$_n$CH$_3$; n = 3 | —(CH$_2$)$_n$CH$_3$; n = 3 |
| 93 | CO(CH$_2$)$_n$CH$_3$; n = 3 | —(CH$_2$)$_n$CH$_3$; n = 4 |
| 94 | CO(CH$_2$)$_n$CH$_3$; n = 3 | —(CH$_2$)$_n$CH$_3$; n = 5 |
| 95 | CO(CH$_2$)$_n$CH$_3$; n = 3 | —(CH$_2$)$_n$CH$_3$; n = 6 |
| 96 | CO(CH$_2$)$_n$CH$_3$; n = 3 | —CH$_2$(CH$_2$)$_n$COCH$_3$; n = 1 |
| 97 | CO(CH$_2$)$_n$CH$_3$; n = 3 | —CH$_2$(CH$_2$)$_n$COCH$_2$CH$_3$; n = 1 |
| 98 | CO(CH$_2$)$_n$CH$_3$; n = 3 | —CH$_2$(CH$_2$)$_n$COCH$_3$; n = 2 |
| 99 | CO(CH$_2$)$_n$CH$_3$; n = 3 | —CH$_2$(CH$_2$)$_n$COCH$_3$; n = 3 |
| 100 | CO(CH$_2$)$_n$CH$_3$; n = 3 | —CH$_2$(CH$_2$)$_n$COCH$_3$; n = 4 |
| 101 | CO(CH$_2$)$_n$CH$_3$; n = 3 | —CH$_2$N$_3$ |
| 102 | CO(CH$_2$)$_n$CH$_3$; n = 3 | —CH$_2$OCOCH$_3$ |
| 103 | CO(CH$_2$)$_n$CH$_3$; n = 3 | —(CH$_2$)$_n$SCOCH$_3$; n = 1 |
| 104 | CO(CH$_2$)$_n$CH$_3$; n = 3 | —(CH$_2$)$_n$SCOCH$_3$; n = 2 |
| 105 | CO(CH$_2$)$_n$CH$_3$; n = 3 | —(CH$_2$)$_n$SCOCH$_3$; n = 3 |
| 106 | CO(CH$_2$)$_n$CH$_3$; n = 3 | —CH$_2$Ph |
| 107 | CO(CH$_2$)$_n$CH$_3$; n = 3 | —CH(CH$_3$)$_2$ |
| 108 | CO(CH$_2$)$_n$CH$_3$; n = 3 | —CH$_2$CF$_3$ |
| 109 | CO(CH$_2$)$_n$CH$_3$; n = 3 | —(CH$_2$)$_3$CH(CH$_3$)$_2$ |
| 110 | CO(CH$_2$)$_n$CH$_3$; n = 3 | —CH$_2$C=CH(CH$_3$) |

Another aspect of the invention is a compound of the invention for use in the treatment or prevention in a subject of a disease, disorder or symptom thereof delineated herein.

Another aspect of the invention is the use of a compound of the invention in the manufacture of a medicament for treatment or prevention in a subject of a disease, disorder or symptom thereof delineated herein.

Figure 1A:
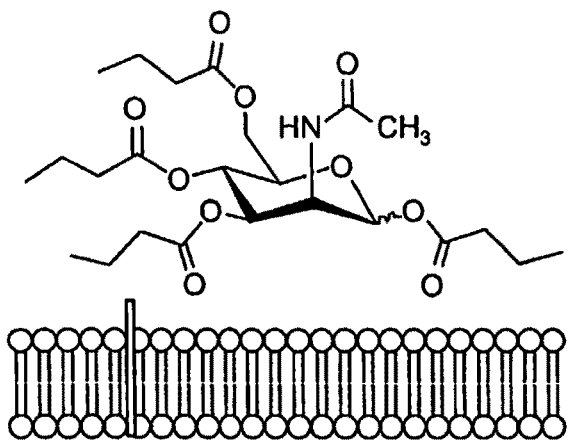
FIG. 1. Synergistic targeting of glycosylation and cell cycle progression.
Figure 1A:
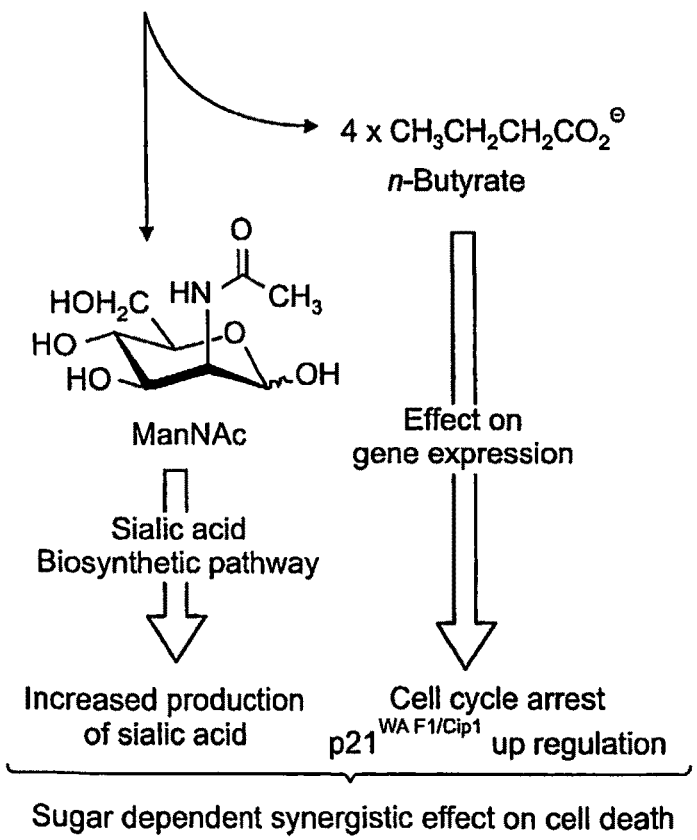
Figure 1B:
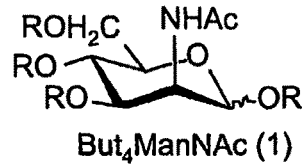
Figure 1B:
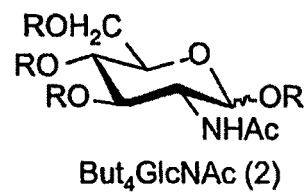
Figure 1B:
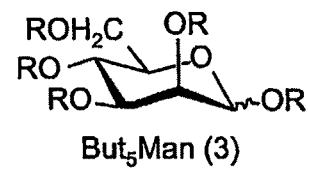
Figure 1B:
Figure 1B:
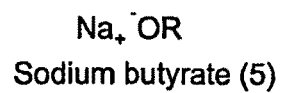

A: Schematic diagram showing the cellular uptake of 1, intracellular release of butyrate and ManNAc and the synergistic activity resulting in cell cycle arrest and apoptosis.

B: Structures of butyrate-carbohydrate hybrid compounds studied in this report.

FIG. 2. Arrest and execution of cancer cells by But$_4$ManNAc (1)

A: Short term (day 3 and 5) and long term (day 15) growth characteristics of Jurkat cells incubated with 1-4; treatment with 1 induces both growth arrest and cell death whereas cells treated with either 2, 3, or 4 resumed cell growth over the long term.

B: Trypan blue cell viability assay of Jurkat cells incubated with 1-3 at 200 μM.

C: Effect of 1-4 on growth characteristics of HL-60 cells on day 15. Standard deviations of three replicate experiments were less than 10% and the error bars were omitted for clarity.

FIG. 3. Effect of sodium butyrate (5) and But$_4$ManNAc (1) on cellular morphology A: HeLa cells display growth of extended processes upon incubation with 1 or 5 for 3 days.

B: AD293 cells showing the toxicity induced by 5 and 1 after incubation for 2 days.

FIG. 4. Up regulation of p21$^{WAF1/Cip1}$ by 1-5

A: Expression of p21$^{WAF1/Cip1}$ promoter-driven luciferase in AD293 (HEK) cells transiently-transfected with luc-p21$^{WAF1/Cip1}$ plasmid and subsequently incubated with 1-4 measured by luminometry.

B: A time course of the endogenous expression of p21$^{WAF1}$ in Jurkat cells treated with 1 or 5 using an anti-p21$^{WAF1}$ antibody and flow cytometry quantification.

C: Comparison of luc-p21$^{WAF1/Cip1}$ expression in AD293 cells treated with either 1 (0-250 μM), 5 (0-10 mM) alone or a mixture of 5 (0-10 mM) and ManNAc (0-2.5 mM) at a relative molar ratio of 4:1. In this set of assays, concentrations of the test compounds were increased until signal-limiting toxicity occurred. Error bars are standard deviation of at least three replicate samples.

FIG. 5. Cell cycle arrest and apoptosis

A: Flow cytometry histograms showing DNA content and cell cycle status of Jurkat cells incubated with 1-4 at 200 μM for five days measured by PI/RNase staining.

B: DNA content of Jurkat cells incubated with 1 at 0-200 μM, for five days, showing dose dependent increase in population of apoptotic cells.

Figure 6A:
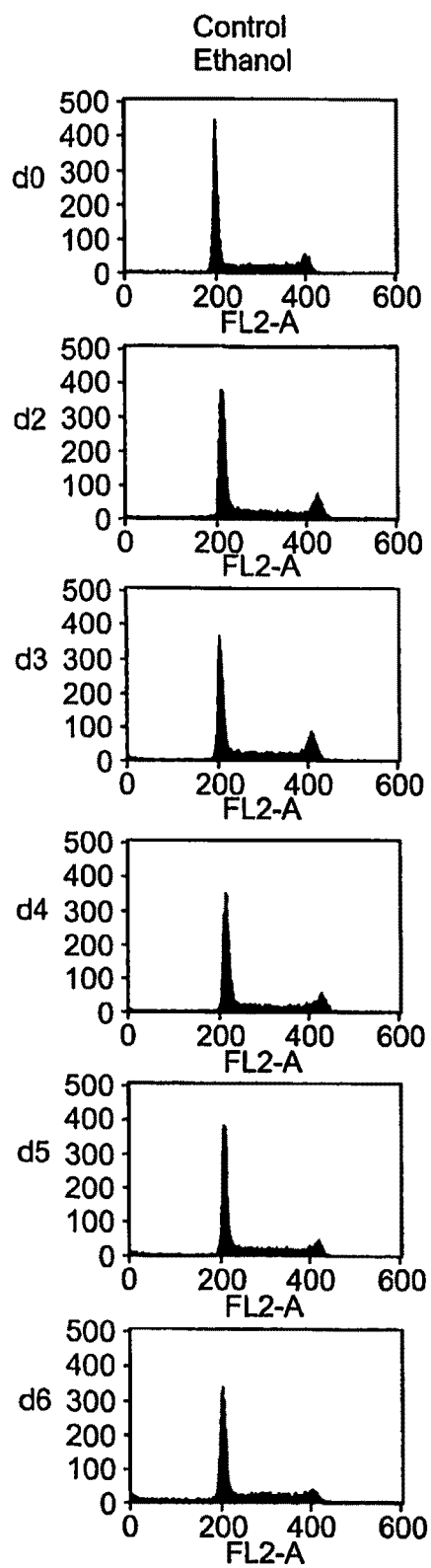
Figure 6B:
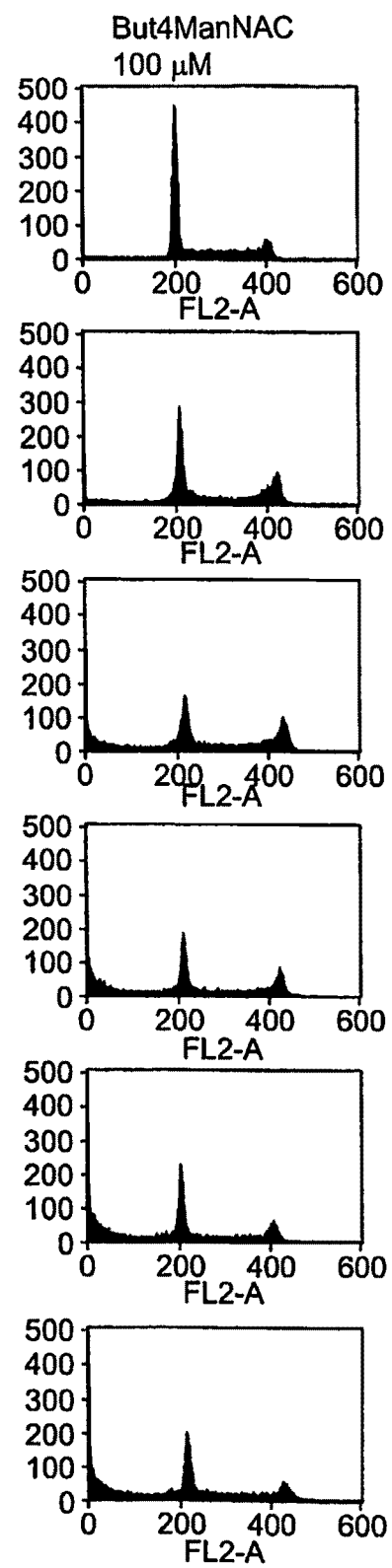
Figure 6C:
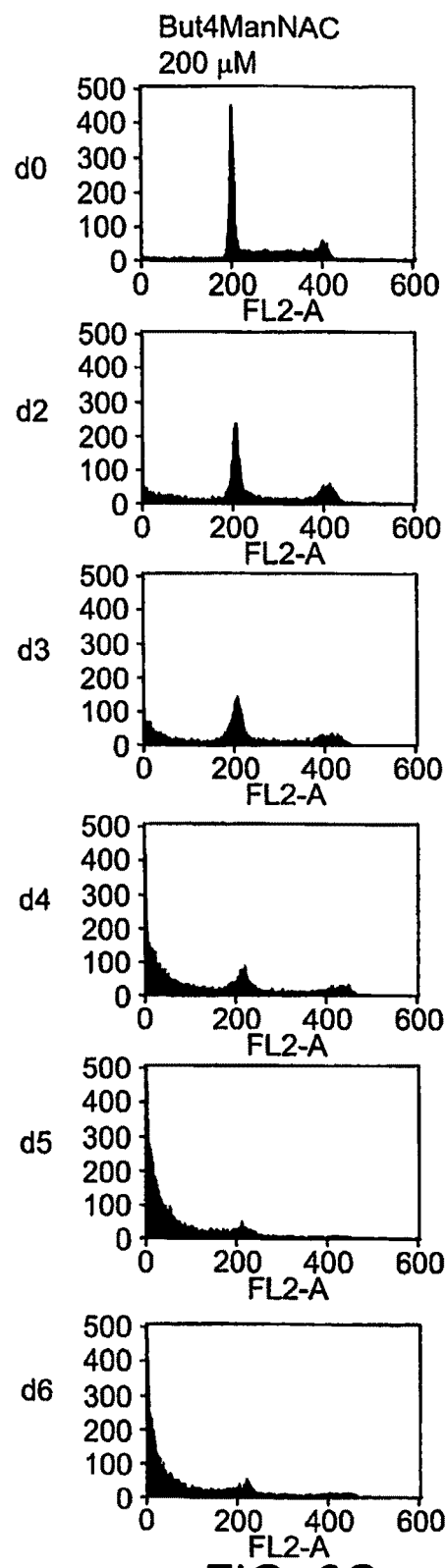

FIG. 6. Time course of cell cycle arrest and cell death

A: Flow cytometry histograms showing DNA content and change in cell cycle status of Jurkat cells over a six day period.

B: DNA content and cell cycle status of Jurkat cells incubated with 1 at 100 μM on day 0 and days 2-6.

C: DNA content and cell cycle status of Jurkat cells incubated with 1 at 200 μM on day 0 and days 2-6.

FIG. 7. Sialic acid biosynthesis in cells incubated with 1, 5, or ManNAc

A: Total sialic acid content, determined by periodate-resorcinol assay, in Jurkat cells incubated with either 1 (0-250 μM), ManNAc (0-10 mM) alone or a mixture of ManNAc (0-5 mM) and 5 (0-20 mM) at a molar ratio of 1:4.

B: Total sialic acid content in Jurkat cells primed for increased sialic acid production by incubation with 0, 50 and 100 mM of ManNAc.

C: Short term growth characteristics of Jurkat cells pre-incubated with ManNAc 50 mM or 100 mM or without ManNAc cultured in the presence of 5 at 0-2.0 mM after five days. Error bars are standard deviation of at least three replicate samples.

D: Long term growth characteristics of Jurkat cells pre-incubated with ManNAc 50 mM or 100 mM or without ManNAc cultured in the presence of 5 at 0-2.0 mM for 15 days. Error bars are standard deviation of at least three replicate samples.

Figure 8:
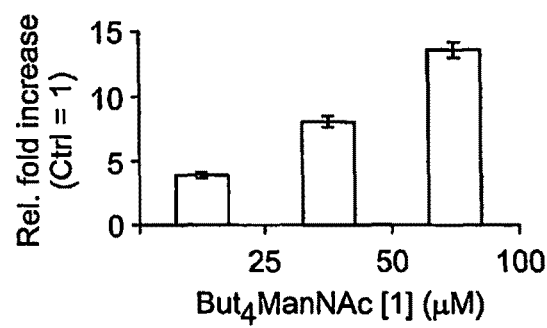

FIG. 8: Caspase-3 activity assay information showing induction of apoptosis

DETAILED DESCRIPTION OF THE INVENTION

ManNAc has several attractive features that led us to select it as an hexosamine for use in butyrate-sugar hybrid drug development. First, it is a committed precursor for the sialic acid biosynthetic pathway and has no other known metabolic roles, thereby allowing a specific and unique biochemical pathway to be targeted (34, 35). Second, uptake of exogenous ManNAc alters flux through the sialic acid biosynthetic pathway (36) and changes sialyltransferase and sialidase activity (37) thereby altering the display of sialic acid on cell surface glycoproteins (38, 39) and glycolipids (40, 41). Because these sialoglycans modulate apoptosis (38-42), we hypothesized that an n-butyrate prodrug with ManNAc as an active carrier would both "arrest" and "execute" cancer cells via SCFA-mediated cell cycle inhibition and ManNAc-augmented apoptosis, respectively (FIG. 1A). Results disclosed herein verify this hypothesis by demonstrating that butyrate gains a unique ability to induce apoptosis when presented to cells as the hybrid molecule "But$_4$ManNAc." It is also confirmed that this molecule has characteristic SCFA activity and activates sialic acid biosynthesis, as expected of each of its functional moieties. In concurrent control experiments, delivery of n-butyrate via other carbohydrate scaffolds only achieved transient inhibition of cell growth and thereby illustrated the necessity of targeting a specific glycosylation pathway—sialic acid biosynthesis—to achieve synergistic toxicity against cancer cells not seen with either the SCFA or sugar functionality alone.

The invention relates to short chain fatty acid (SCFA)-hexosamine hybrid molecules that target both histone deacetylation and glycosylation pathways to achieve synergistic killing modalities against human cancer cells. Specifically, n-butyrate esters of N-acetyl-D-mannosamine (But$_4$ManNAc) efficiently induced apoptosis whereas corresponding esters of N-acetyl-D-glucosamine (But$_4$GlcNAc), D-mannose (But$_5$Man), or D-glycerol (tributyrin) only provided transient cell cycle arrest. These findings establish that n-butyrate, when delivered to cells via any carbohydrate scaffold, can function as a histone deacetylase inhibitor (HDACi), up-regulate p21$^{WAF1/Cip1}$-driven gene expression, and inhibit proliferation. However only But$_4$ManNAc, a compound that primes sialic acid biosynthesis in addition to functioning as an HDACi, ultimately killed the cells thereby demonstrating that the core sugar moiety plays a key role in augmenting the bioactivity of butyrate. Post translational O-GlcNAc modification of proteins at serine/threonine side chains:

The cytoplasmic and nuclear proteins are modified post-translationally by phosphorylation and glycosylation at the amino acid side chains which act as triggers of signal transduction. The O-GlcNAc (N-acetyl-D-glucosamine) modification is found on the same serine residue under certain conditions that are also modified by phosphorylation at other conditions, known as the 'ying-yang' hypothesis (ref: Zachara, N. E., Hart, G. W., Chem. Rev. 102, 431-438 (2002). The emerging significance of O-GlcNAc in cellular regulation; 2. Slawson, C., Housley, M. P., Hart, G. W., J. Cell Biochem. 97, 71-83 (2006). O-GlcNAc cycling: how a single sugar post-translational modification is changing our understanding about signaling networks.

Protein phosphorylation is a key event in many signaling events. O-GlcNAc attachment can prevent or compete with protein phosphorylation and hence regulate signaling networks. Cellular O-GlcNAc modification level is up regulated under stress conditions (heat, toxic metal, oxidative stress) and is generally considered as a pro-survival mechanism of cells.

External delivery of GlcNAc can increase levels of protein O-GlcNAc modification, but, the intracellular delivery of the hydrophilic free monosaccharide GlcNAc is inefficient, usually requiring millimolar quantities. The novel hydrophobic analog 'But$_4$GlcNAc' reported here can enhance cellular uptake and act as an efficient prodrug for GlcNAc, requiring only micromolar levels.

I. Diseases, Disorders and Symptoms Thereof

As noted, diseases, disorders or symptoms thereof of specific interest include cancer, those wherein proliferation may be implicated. Specifically, cancers or proliferative disorders include breast, prostate, lung, colon, liver, solid tumor, myeloma, leukemia, bladder, stomach, and the like; diseases, disorders or symptoms thereof, or diseases, disorders or symptoms thereof wherein targets and/or substrates associated with the diseases, disorders or symptoms thereof are mediated by cell cycle inhibition (e.g., HDAC inhibition) and/or abnormal glycosylation modulation (e.g., sialic acid biosynthesis).

II. Compounds

Another aspect is a radio labeled compound of any of the formulae delineated herein. Such compounds have one or more radioactive atoms or heavy atom isotopes (e.g., $^3$H, $^2$H, $^{14}$C, $^{13}$C, $^{35}$S, $^{125}$I, $^{131}$I, $^{18}$O, $^{17}$O, $^{19}$F for PET applications) introduced into the compound. Such compounds are useful for drug metabolism studies and diagnostics.

As used herein, the term "alkyl" refers to a straight-chained or branched hydrocarbon group containing 1 to 18 (e.g., C1-C-18, inclusive; and any sub-range thereof) carbon atoms. The term "lower alkyl" refers to a C1-C6 alkyl chain. Examples of alkyl groups include methyl, ethyl, n-propyl, isopropyl, n-butyl, sec-butyl, tert-butyl, pentyl(n-, sec-, tert-), and pivaloyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The sp$^2$ or sp carbons of an alkenyl group and an alkynyl group, respectively, may optionally be the point of attachment of the alkenyl or alkynyl groups.

The term "alkoxy" refers to an —O-alkyl substituent group. The term "ester" refers to a —C(O)O—R, wherein R is as defined herein. An "amido" is an —C(O)NH$_2$, and an "N-alkyl-substituted amido" is of the formula C(O)NHR, wherein R is as defined herein.

The term "mercapto" refers to a —SH group.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, difluoromethyl, bromomethyl, 1,2-dichloroethyl, 4-iodobutyl, 2-fluoropentyl, and the like. The term "perhaloalkyl" refers to a alkyl group in which all hydrogen atoms are replaced by a halo group (e.g., trifluoromethyl, pentafluoroethyl).

The term "cycloalkyl" refers to a hydrocarbon 3-8 membered monocyclic or 7-14 membered bicyclic ring system having at least one non-aromatic ring. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cycloalkenyl" refers to a hydrocarbon 3-8 membered monocyclic or 7-14 membered bicyclic ring system having at least one non-aromatic ring, wherein the non-aromatic ring has some degree of unsaturation. Cycloalkenyl groups may be optionally substituted with one or more substituents. In one embodiment, 0, 1, 2, 3, or 4 atoms of each ring of a cycloalkenyl group may be substituted by a substituent. Examples of cycloalkenyl groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocycle, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "arylalkyl" means an aryl group that is attached to another group by a (C$_1$-C$_6$)alkylene group. Arylalkyl groups may be optionally substituted, either on the aryl portion of the arylalkyl group or on the alkylene portion of the arylalkyl group, with one or more substituent. Representative arylalkyl groups include benzyl, 2-phenyl-ethyl, naphth-3-yl-methyl and the like.

As used herein, the term "alkylene" refers to an alkyl group that has two points of attachment. The term "(C$_1$-C$_6$)alkylene" refers to an alkylene group that has from one to six carbon atoms. Non-limiting examples of alkylene groups include methylene (—CH$_2$—), ethylene (—CH$_2$CH$_2$—), n-propylene (—CH$_2$CH$_2$CH$_2$—), isopropylene (—CH$_2$CH (CH$_3$)—), and the like.

The term "arylalkoxy" refers to an alkoxy substituted with aryl.

The term "heteroaryl" refers to an aromatic monocyclic, bicyclic, or tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a ($C_1$-$C_6$)alkane or alkene. Heteroarylalkyl groups may be optionally substituted, either on the heteroaryl portion of the heteroaralkyl group or on the alkyl portion of the heteroarylalkyl group, with one or more substituents. Representative heteroaralkyl groups include 2-(pyridin-4-yl)-propyl, 2-(thien-3-yl)-ethyl, imidazol-4-yl-methyl and the like.

The term "heterocycloalkyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl, thiirene.

The term "heterocycloalkenyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclyl groups may be optionally substituted with one or more substituents. In one embodiment, 0, 1, 2, 3, or 4 atoms of each ring of a heterocyclyl group may be substituted by a substituent. Examples of these groups include 2-pyrrolinyl, 3-pyrrolinyl, 4H-pyranyl, 2-pyrazolinyl, dihydrofuranyl, dihydrothiophenyl, 2-imidazolinyl, indolinyl and the like.

The term "alkylamino" refers to an amino substituent which is further substituted with one or two alkyl groups. The term "aminoalkyl" refers to an alkyl substituent which is further substituted with one or more amino groups. The term "mercaptoalkyl" refers to an alkyl substituent which is further substituted with one or more mercapto groups. The term "hydroxyalkyl" refers to an alkyl substituent which is further substituted with one or more hydroxyl groups. The term "sulfonylalkyl" refers to an alkyl substituent which is further substituted with one or more sulfonyl groups. The term "sulfonylaryl" refers to an aryl substituent which is further substituted with one or more sulfonyl groups. The term alkylcarbonyl refers to an—C(O)-alkyl. The term "mercaptoalkoxy" refers to an alkoxy substituent which is further substituted with one or more mercapto groups.

The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, cyclyl, heterocycloalkyl, or heterocyclyl group) is replaced with any desired group that does not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), or imino (=NR), wherein R is as defined herein.

In other embodiments, substituents on any group (such as, for example, alkyl, alkenyl, alkynyl, aryl, arylalkyl, heteroaryl, heteroaralkyl, cycloalkyl, cycloalkenyl, heterocycloalkyl, and heterocycloalkenyl) can be at any atom of that group, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocycloalkenyl, heterocycloalkyl, arylalkyl, heteroarylalkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents on alkyl, alkenyl, alkynyl, aryl, aralkyl, heteroaryl, heteroaralkyl, cycloalkyl, cyclyl, heterocycloalkyl, and heterocyclyl include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, (=O), (=S), (=$NR^{15}$), $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)H$, $C(O)R^{17}$, $NR^{15}C(O)R^{17}$, $Si(R^{15})_3$, $OSi(R^{15})_3$, $Si(OH)_2R^{15}$, $P(O)(OR^{15})_2$, $S(O)R^{17}$, or $S(O)_2R^{17}$. Each $R^{15}$ is independently hydrogen, $C_1$-$C_6$ alkyl optionally substituted with cycloalkyl, aryl, heterocyclyl, or heteroaryl. Each $R^{16}$ is independently hydrogen, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, COOH, C(O)O$C_1$-$C_4$ alkyl, $NH_2$, $C_1$-$C_4$ alkylamino, or $C_1$-$C_4$ dialkylamino.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating diseases, disorders, or symptoms thereof, including those delineated herein). The compounds produced by the methods herein can be incorporated into compositions, including solutions, capsules, crèmes, or ointments for administration to a subject (e.g., human, animal). Such compositions (e.g., pharmaceuticals) are useful for providing to the subject desirable health or other physiological benefits that are associated with such compounds.

The compounds of the formulae herein are available from commercial sources or may be synthesized using reagents and techniques known in the art, including those delineated herein. The chemicals used in the synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds of this invention include the compounds themselves, as well as their salts, solvate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited, to sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucuronate, saccharate, formate, benzoate, glutamate, methanesulfonate, ethanesulfonate, benzenesulfonate, and p-toluenesulfonate salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, oxalic acid, benzoic acid, glutamic acid, methanesulfonic acid, ethanesulfonic acid, benzenesulfonic acid, and p-toluenesulfonic acid.

As used herein, the term "hydrate" means a compound of the present invention or a salt thereof, which further includes a stoichiometric or non-stoichiometric amount of water bound by non-covalent intermolecular forces.

III. Methods of Treatment

In one embodiment, the present invention provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a cancer or proliferative disease or cancer metastasis, or disorder or symptom thereof. The method includes the step of administering to the mammal a therapeutic amount of an amount of a compound herein sufficient to treat the disease or disorder or symptom thereof, under conditions such that the disease or disorder is treated.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The preferred therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a cancer or proliferative disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which cell proliferation and migration may be implicated.

For therapeutic applications, the compounds of the formulae herein may be suitably administered to a subject such as a mammal, particularly a human, alone or as part of a pharmaceutical composition, comprising the formulae herein together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, and references cited therein).

A skilled artisan will recognize that in addition to tablets, other dosage forms can be formulated to provide slow or controlled release of the active ingredient. Such dosage forms include, but are not limited to, capsules, granulations and gel-caps.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

Other applications of compounds of the formulae herein are for treatment of stem cells in vitro to induced directed and controlled differentiation and subsequent applications in regenerative medicine and cell transplantation therapy etc. The compound and compositions herein are administered (e.g., introduced to, contacted) with stem cells in a therapeutically effective amount in order to induce the desired effect. See, e.g., Sampathkumar et al., *Nature Chemical Biology*, vol. 2,. No. 3, pp. 149-152 (March 2006). In particular, the compounds are useful for cellular response processes including for example, in modulating neuronal differentiation, inducing β-catenin expression, and modulating glycosylation pathways.

As used herein, the terms "HDAC inhibitor compound derivative" and "HDAC inhibitor prodrug" are those based on compounds (including those of the formulae delineated herein) and include pharmaceutically acceptable derivatives or prodrugs thereof, respectively. A "pharmaceutically acceptable derivative or prodrug" means any pharmaceutically acceptable salt, ester, salt of an ester, or other derivative of a compound of this invention which, upon administration to a recipient, is capable of providing (directly or indirectly) an active compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214; Testa, B. and Mayer, J. M. *Hydrolysis in Drug and Prodrug Metabolism, Chemistry, Biochemistry and Enzymology*, VHCA, Zürich and Wiley-VCH GmbH & Co. KGaA, Weihnheim, 2003.

The compounds of this invention may be modified by appending appropriate functionalities to enhance selective biological properties. Such modifications are known in the art and include those which increase biological penetration into a given biological compartment (e.g., central nervous system), increase oral availability, increase solubility to allow administration by injection, alter metabolism and alter rate of excretion. It will be appreciated that actual preferred amounts of a given compound herein used in a given therapy will vary according to the particular active compound being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests, or by any method known in the art or disclosed herein.

The compounds herein may contain one or more asymmetric centers and thus occur as racemates and racemic mixtures, single enantiomers, individual diastereomers and diastereomeric mixtures. All such isomeric forms of these compounds are expressly included in the present invention. The compounds herein may also contain linkages (e.g., carbon-carbon bonds) wherein bond rotation is restricted about that particular linkage, e.g., restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. The term "N-oxides" refers to one or more nitrogen atoms, when present in an aromatic ring nitrogen-containing compound, that are in N-oxide oxidation form, i.e., N→O.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein.

Preferably, a tissue or fluid sample is first removed from a subject. Examples of suitable samples include blood, mouth or cheek cells, and hair samples containing roots. Other suitable samples would be known to the person skilled in the art. Determination of protein levels, glycolipid (gangliosides) levels (by HPTLC) and/or mRNA levels (e.g., Marker levels) in the sample can be performed using any suitable technique known in the art, including, but not limited to, enzyme immunoassay, ELISA, radiolabelling/assay techniques, blotting/chemiluminescence methods, real-time PCR, and the like.

Therefore, in certain embodiments, compounds of the invention, such as those of the formulae herein, are administered at dosage levels of about 0.0001 to 4.0 grams once per day (or multiple doses per day in divided doses) for adults. Thus, in certain embodiments of this invention, a compound herein is administered at a dosage of any dosage range in which the low end of the range is any amount between 0.1 mg/day and 400 mg/day and the upper end of the range is any amount between 1 mg/day and 4000 mg/day (e.g., 5 mg/day and 100 mg/day, 150 mg/day and 500 mg/day). In other embodiments, a compound herein, is administered at a dosage of any dosage range in which the low end of the range is any amount between 0.01 mg/kg/day and 90 mg/kg/day and the upper end of the range is any amount between 1 mg/kg/day and 100 mg/kg/day (e.g., 0.5 mg/kg/day and 2 mg/kg/day, 5 mg/kg/day and 20 mg/kg/day, 50-150 mg/kg/day). The dosing interval can be adjusted according to the needs of individual patients. For longer intervals of administration, extended release or depot formulations can be used.

In one embodiment, the invention provides a method of monitoring treatment progress. The method includes the step of determining a level of diagnostic marker (Marker) (e.g., any target delineated herein modulated by a compound herein) or diagnostic measurement (e.g., screen, assay) in a subject suffering from or susceptible to a disorder or symptoms thereof associated with disease (e.g., cancer or other disease herein), in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level; and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment. The comparison of marker levels is reported by a clinic, laboratory, or hospital agent to a health care professional. When the level of marker prior to administration of the compound to the subject is lower (or higher depending on the function being assessed) than the level of marker subsequent to administration of the compound to the subject, then the amount of compound administered to the subject is an effective amount.

In other method embodiments, the levels of metabolites from the inhibitor compounds can assessed. For example, the methods can further include assessment of levels of inhibitors or inhibitor derivatives (or metabolites thereof) resulting from the inhibitor compounds or inhibitor derivative compounds, including those of the formulae herein. Parameters such as the subject identification or selection for the treatment regimen, treatment efficacy, treatment protocol status or dosage range can be determined using these measurements.

IV. Kits

The invention also provides kits for treatment or prevention of a disease or disorder (or symptoms) thereof, including cancer, or proliferative disorder or symptom thereof. In one embodiment, the kit includes an effective amount of a compound herein in unit dosage form, together with instructions for administering the compound to a subject suffering from or susceptible to a disease or disorder or symptoms thereof. In other embodiments, the kit comprises a sterile container which contains the compound; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the compound of the formulae herein for treatment of a disease or disorder or symptoms thereof, including those of a cardiovascular nature. In other embodiments, the instructions include at least one of the following: description of the compound; dosage schedule and administration for treatment of a disease or disorder or symptoms thereof, including those of a cardiovascular nature; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

This is the first report evaluating the effects of the compounds herein on several stages of cancer development and treatment. The prevention and treatment methods are contemplated to reduce apoptosis of normal (e.g., non-cancerous cells or tissue) or to sensitize cancerous cells or tissue to be more vulnerable to the compounds themselves or when co-administered with additional anticancer agents.

Combinations of substituents and variables envisioned by this invention are only those that result in the formation of stable compounds. The term "stable", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition that has been linked to proliferation, cell cycle inhibition (e.g., HDAC inhibition) and/or abnormal glycosylation modulation (e.g., sialic acid biosynthesis).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The invention will be further described in the following examples. It should be understood that these examples are for illustrative purposes only and are not to be construed as limiting this invention in any manner.

EXAMPLES

Synthesis of Butyrate-Sugar Compounds

All reagents and solvents were commercial grade and used without further purification. Sodium n-butyrate (5) was purchased from Sigma (St. Louis, Mo.) and tributyrin (4) from Acros Organics. Melting points were uncorrected. NMR ($^1$H and $^{13}$C) were recorded on a Varian Unity 400 MHz FT-NMR spectrometer. MALDI-TOF spectra were recorded on a Voyager DE-STR (Applied Biosystems) instrument. The samples were prepared in super-DHB matrix in 50% aqueous $CH_3CN$. Elemental analysis was performed by Atlantic Microlab, Inc. (Norcross, Ga.). Column chromatography was performed using silica gel (60 Å). TLC was performed using fluorescent silica gel (250 µm) coated glass plates. But$_4$ManNAc (1) was synthesized as previously reported. The novel analogs But$_4$GlcNAc (2) and But$_5$Mannose (3) (α- and β-anomers) were synthesized and characterized as described below.

General Procedure for the Preparation of Peracylated ManNAc derivatives. To a stirred solution of N-acetyl-D-mannosamine (ManNAc) monohydrate (0.53 g, 2.2 mmol) in pyridine (2.0 mL) at 21° C. was added the corresponding anhydride (15.6 mmol) and DMAP (cat.). After 24 h the mixture was concentrated under vacuum and co-concentrated with toluene (25 mL). The residue was dissolved in methylene chloride (100 mL), washed with cold aqueous HCl (0.5 N, 100 mL), water (100 mL) and saturated $NaHCO_3$ (100 mL). The organic layer was filtered and concentrated. Column chromatography of the residue (hexanes/ethyl acetate) on silica gel provided the corresponding per-acyl compounds in the form of syrups that crystallized upon standing.

2-Acetylamino-2-deoxy-1,3,4,6-tetra-O-butanoyl-α, β-D-mannopyranoside (But$_4$ManNAc) (1)

(0.94 g, 87%); R$_f$ 0.4 (hexanes:ethyl acetate 2:1); NMR (CDCl$_3$) (400 MHz) $^1$H δ (mixture of anomers, α/β~10/90) 6.03 (d, 0.1H, J=1.7), 5.87 (d, 0.9H, J=1.6), 5.76 (d, 1H, J=9.3), 5.34 (dd, 0.1H, J=10.4, J=4.6), 5.18 (t, 0.1H, J=10.2), 5.13 (t, 0.9H, J=9.8), 5.06 (dd, 0.9H, J=9.9, J=4.0), 4.75 (ddd, 0.9H, J=9.1, 3.8, 1.7), 4.63 (ddd, 0.1H, J=9.3, J=4.4, J=1.9), 4.27 (dd, 0.9H, J=12.4, J=5.4), 4.23 (dd, 0.1H, J=12.6, J=5.2), 4.09 (dd, 0.9H, J=12.4, J=2.4), 4.05 (m, 0.1H), 4.01 (m, 0.1H), 3.80 (ddd, 0.9H, J=9.4, J=5.5, J=2.4), 2.39-2.14 (m, 8H), 2.07 (s, 3H), 1.70-1.53 (m, 8H), 0.99-0.87 (m, 12H); $^{13}$C NMR (100 MHz) δ 173.0, 172.5, 172.3, 170.9, 170.7; 170.4, 91.5, 90.5 ($^1J_{C1-H1}$=165), 73.5, 71.1, 70.3, 68.6, 65.0, 61.8, 61.6, 49.6, 49.4, 35.8, 35.7, 23.3, 18.3, 18.2, 18.0, 17.9, 13.6, 13.5, 13.5, 13.4; FAB-MS m/z 524 [(M+Na)$^+$]; Anal. Calcd for $C_{24}H_{39}NO_{10}$: C, 57.47; H, 7.84. Found: C, 57.35; H, 7.77.

2-Acetamido-1,3,4,6-tetra-O-butanoyl-2-deoxy-α-D-glucopyranose (But$_4$GlcNAc) (2)

To a stirred mixture of N-acetyl-D-glucosamine (1.03 g, 4.7 mmol) in pyridine (4.0 mL) and butyric anhydride (4.0 mL, 24.5 mmol) at 22° C. was added DMAP (cat.). After 60 h, the reaction mixture was co-concentrated with toluene (3×10 mL). The residue was dissolved in $CH_2Cl_2$ (100 mL), washed with dilute HCl (100 mL), water (100 mL) and saturated aqueous $NaHCO_3$ (100 mL). The organic layer was dried ($Na_2SO_4$), filtered and concentrated. Column chromatography (ethyl acetate-hexanes) of the residue gave pure α-anomer (0.5 g, 21%) of 2 as a solid. M.p. 152-154° C.; NMR (CDCl$_3$) $^1$H-NMR (400 MHz): δ 6.18 (d, 1H, J=3.8), 5.55 (d, 1H, J=9.0), 5.25 (t, 1H, J=9.5), 5.21 (t, 1H, J=9.5), 4.46 (ddd, 1H, J=9.0, J=3.6, J=1.8), 4.18 (dd, 1H, J=12.4, J=4.5), 4.07 (dd, 1H, J=12.5, J=2.2), 3.96 (ddd, J=9.6, J=4.3, J=2.1), 2.40 (t, 2H, J=7.2), 2.33-2.22 (m, 6H), 1.90 (s, 3H), 1.73-1.55 (m, 8H), 1.00-0.88 (m, 12H); $^{13}$C-NMR (100 MHz): δ 174.4, 173.2, 171.6, 171.3, 169.8, 90.4, 70.3, 70.0, 67.1, 61.4, 51.2, 36.0 (4C), 35.8, 23.0, 18.4 (2C), 18.3, 18.2, 13.6 (2C), 13.5 (3C); MALDI-MS (m/z): [M+Na]$^+$calcd for $C_{24}H_{39}NNaO_{10}$, 524.2466; found, 524.2392; Analysis (calcd, found for $C_{24}H_{39}NO_{10}$): C (57.47, 57.26), H (7.84, 7.84).

1,2,3,4,6-Penta-O-butanoyl-α,β-D-mannopyranose (But$_5$Mannose) (3)

To a stirred mixture of D-mannose (0.76 g, 4.2 mmol) in pyridine (4.0 mL) and butyric anhydride (4.0 mL, 24.5 mmol) at 22° C. was added DMAP (cat.). After 48 h, the reaction mixture was co-concentrated with toluene (3×10 mL). The residue was dissolved in $CH_2Cl_2$ (100 mL), washed with dilute HCl (100 mL), water (100 mL) and saturated aqueous $NaHCO_3$ (100 mL). The organic layer was dried ($Na_2SO_4$), filtered and concentrated. Column chromatography (ethyl acetate-hexanes) of the residue gave pure α- (1.4 g, 62%) and β- (0.5 g, 22%) anomers of 1 as oil.

1,2,3,4,6-Penta-O-butanoyl-α-D-mannopyranose (α-But$_5$Mannose): NMR (CDCl$_3$) $^1$H-NMR (400 MHz): δ 6.08 (d, 1H, J=2.0), 5.38 (t, 1H, J=10.2), 5.34 (dd, 1H, J=10.1, J=34), 5.27 (dd, 1H, J=2.9, J=2.0), 4.21 (dd, 1H, J=12.4, J=5.0), 4.12 (dd, 1H, J=12.4, J=2.1), 4.02 (ddd, 1H, J=9.2, J=4.9, J=2.1), 2.41-2.17 (m, 10H), 1.74-1.52 (m, 10H), 1.00-0.87 (m, 15H); $^{13}$C-NMR (100 MHz): δ 173.1, 172.5, 172.2, 172.0, 170.7, 90.4 ($^1J_{C-H}$=177), 70.8, 68.7, 68.1, 65.1, 61.8, 35.9 (4C), 35.8, 18.4, 18.3, 18.2 (2C), 18.2, 13.6, 13.5 (4C); MALDI-MS (m/z): [M+Na]$^+$calcd for $C_{26}H_{42}NaO_{11}$, 553.2619; found, 553.2326; Analysis (calcd, found for $C_{26}H_{42}O_{11}$): C (58.85, 58.79), H (7.98, 8.19).

1,2,3,4,6-Penta-O-butanoyl-α-D-mannopyranose (α-But$_5$Mannose): NMR (CDCl$_3$) $^1$H-NMR (400 MHz): δ 5.87 (d, 1H, J=1.3), 5.48 (dd, 1H, J=3.4, J=1.0), 5.31 (t, 1H, J=9.9), 5.14 (dd, 1H, J=9.9, J=3.4), 4.25 (dd, 1H, J=12.4, J=5.3), 4.15 (dd, 1H, J=12.4, J=2.3), 3.79 (ddd, 1H, J=9.8, J=5.2, J=2.3), 2.42 (t, 2H, J=6.8), 2.33-2.16 (m, 8H), 1.75-1.51 (m, 10H), 1.01-0.86 (m, 15H); $^{13}$C-NMR (100 MHz): δ 173.1, 172.6, 172.3, 172.1, 171.0, 90.2 ($^1J_{C-H}$=163), 73.3, 70.5, 68.0, 65.1, 61.8, 35.9 (2C), 35.8, 35.7, 35.6, 18.5, 18.2 (2C), 18.1, 17.9, 13.6, 13.5 (3C), 13.4; MALDI-MS (m/z): [M+Na]$^+$calcd for $C_{26}H_{42}NaO_{11}$, 553.2619; found, 553.5510; Analysis (calcd, found for $C_{26}H_{42}O_{11}$): C (58.85, 59.06), H (7.98, 8.12).

Compound No. 45 in Table A.

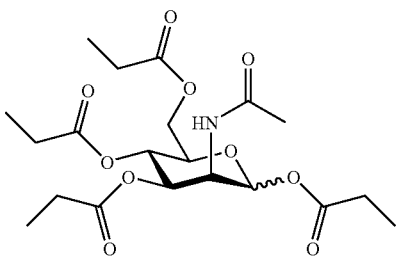

Synthesis as given under general procedure;

2-Acetylamino-2-deoxy-1,3,4,6-tetra-O-propanoyl-α,β-D-mannopyranoside (Prop$_4$ManNAc): (1.0 g, 99%); R$_f$ 0.3 (hexanes:ethyl acetate 1:1); NMR (CDCl$_3$) (400 MHz) $^1$H δ (mixture of anomers, α/β~10/90) 6.03 (d, 0.1H, J=1.6), 5.87 (d, 0.9H, J=2.0), 5.78 (d, 1H, J=9.1), 5.34 (dd, 0.1H, J=10.2, J=4.6), 5.18 (t, 0.1H, J=10.0), 5.13 (t, 0.9H, J=9.6), 5.07 (dd, 0.9H, J=9.8, J=3.8), 4.75 (ddd, 0.9H, J=9.2, J=3.8, J=1.8), 4.62 (ddd, 0.1H, J=9.3, J=4.4, J=1.8), 4.29 (dd, 0.9H, J=12.4, J=5.4), 4.26 (dd, 0.1H, J=11.3, J=5.2), 4.11-4.07 (m, 1H), 4.03 (m, 0.1H), 3.81 (ddd, 0.9H, J=9.2, J=5.3, J=2.4), 2.43- 2.20 (m, 8H), 2.06 (s, 2.7H), 2.05 (s, 0.3H), 1.20-1.05 (m, 12H); $^{13}$C NMR (100 MHz) δ 173.9, 173.3, 173.2, 171.8, 171.1, 170.4, 169.9, 91.6, 90.6 ($^1J_{C1-H1}$=166), 73.5, 71.1, 68.7, 65.2, 65.1, 61.7, 60.4, 49.6, 49.4, 27.4, 27.3, 27.2, 23.3, 21.0, 14.2, 9.0, 8.9, 8.7, 8.5; FAB-MS m/z 468 [(M+Na)$^+$]; Anal. Calcd for $C_{20}H_{31}NO_{10}$: C, 53.92; H, 7.01. Found: C, 53.89; H, 7.10.

Compound No. 31 in Table A

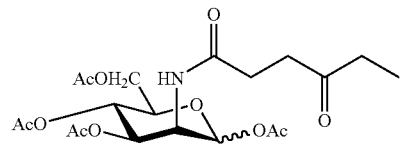

1,3,4,6-Tetra-O-acetyl-N-(4-oxo-hexanoyl)-D-mannosamine (mixture of anomers) (Ac$_4$ManNHomo-Lev). To a solution of 2.6 mL (19 mmol) of triethylamine in 56 mL of anhydrous THF was added 2.47 g (19 mmol) of 4-oxo-hexanoic acid (Sigma Aldrich, Milwaukee Wis.). The reaction was stirred for 15 min at rt under a $N_2$ atmosphere after which 2.4 mL (19 mmol) of isobutyl chloroformate was added drop wise by a syringe. The reaction was stirred for 3.0 h during which time a white precipitate formed. The 4-oxo-hexanoic acid carbonic anhydride was used in the next step without further purification. To a solution of 3.6 g (17 mmol) of mannosamine hydrochloride in 112 mL of 1:1 $H_2O$/THF was added 3.1 mL (22 mmol) of triethylamine. The solution was stirred for 15 min at rt after which the 4-oxo-hexanoic acid carbonic anhydride was added drop wise by an addition funnel. The reaction was stirred for another 36 h under a $N_2$ atmosphere and the solution was concentrated in vacuo. The crude compound was acetylated by treatment with 40 mL of 2:1 Pyr/Ac$_2$O. The reaction was stirred for 12 h at rt and then the solution was concentrated in vacuo. The resulting syrup was washed with 1.0 M HCl (2×30 mL) and saturated $NaHCO_3$ (1×30 mL), then dried over $Na_2SO_4$. Purification of the crude compound by silica gel chromatography yielded a white foam.

$^1$NMR (CDCl$_3$) (500 MHz) $^1$H δ 6.36 (d, 1H, J=9.3), 6.25 (d, 1H, J=9.1), 6.01 (app d, 1H, J=1.7), 5.83 (app d, 1H, J=1.8), 5.28 (dd, 1H, J=10.1, J=4.5), 5.15 (app t, 1H, J=10.1), 5.09 (app t, 1H, J=9.5), 5.01 (dd, 1H, J=9.7, J=4.1), 4.72 (ddd, 1H, J=9.2, J=4.0, J=1.8), 4.58 (ddd, 1H, J=9.3, J=4.4, J=1.8), 4.27 (dd, 1H, J=12.4, J=5.3), 4.26 (dd, 1H, J=12.4, J=4.8), 4.12 (dd, 1H, J=12.4, J=2.6), 4.06 (dd, 1H, J=12.4, J=2.4), 4.01 (ddd, 1H, J=10.0, J=4.6, J=2.4), 3.78 (ddd, 1H, J=9.3, J=5.1, J=2.7), 2.82-2.71 (m, 4H), 2.63-2.56 (m, 2H), 2.52-2.41 (m, 6H), 2.15, 2.13, 2.12, 2.11, 2.04, 2.03, 1.98, 1.97 (8 s, 3H each), 1.06 (t, 3H, J=7.3), 1.05 (t, 3H, J=7.3); $^{13}$C NMR (125 MHz) δ 210.8, 210.5, 173.1, 172.6, 170.2, 169.7, 168.7, 168.4, 91.9, 90.8, 73.5, 71.4, 70.3, 69.2, 65.6, 65.5, 62.2, 62.1, 49.3, 37.6, 37.5, 36.1, 30.2, 30.1, 21.0, 21.0, 20.9, 20.9, 20.8, 8.0; HR-MS (FAB$^+$) Calcd. For $C_{20}H_{29}LiNO_{11}$ [(M+Li)$^+$] 466.1741; Found 466.1904.

Compound No. 37 in Table A

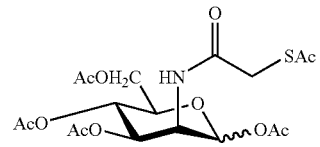

1,3,4,6-Tetra-O-acetyl-2-acetylthioacetamido-2-deoxy-α-D-mannopyranose (Ac₅ManNTGc)

To a stirred suspension of 1,3,4,6-tetra-O-acetyl-2-amino-2-deoxy-α-D-manno-pyranose oxalate (1) (1.0 g, 2.3 mmol) [Ref: Angelino, N. J., Bernacki, R. J., Sharma, M., Doson-Simmons, O. & Korytnyk, W. Versatile intermediates in the selective modification of the amino function of 2-amino-2-dexoy-D-mannopyranose and the 3-position of 2-acetamido-2-deoxy-D-mannose: potential membrane modification in neoplastic control. *Carbohydr Res* 276, 99-115 (1995)] and N-(3-dimethylaminopropyl)-N'-ethylcarbodiimide hydrochloride (EDC) (4.7 mmol, 2.0 equiv) in DMF (20 mL) at 22° C. was added a solution of acetylthioacetic acid (4.7 mmol, 2.0 equiv) [Ref: Gooch, J. & Hawtrey, A. O. Synthesis of thiol-containing analogues of puromycin and a study of their interaction with N-acetylphenylalanyl-transfer ribonucleic acid on ribosomes to form thioesters. *Biochem J* 149, 209-220 (1975)] in DMF (10 mL). After 10 min the mixture was cooled to 0° C. and treated drop wise with triethylamine (1.3 mL, 4.0 equiv). After 24 h the mixture was concentrated and the residue was extracted with $CH_2Cl_2$ (100 mL) and dilute $NaHCO_3$ (100 mL). The aqueous layer was extracted with $CH_2Cl_2$ (2×50 mL). The combined organic layers were dried ($Na_2SO_4$), filtered and concentrated. Column chromatography (hexanes—ethyl acetate) of the residue gave pure α-anomer of 1 (0.79 g, 74%) as a crystalline solid. M.p.: 85-87° C.; NMR ($CDCl_3$) $^1$H-NMR (400 MHz): δ 6.79 (d, J=10.1, 1H), 6.01 (d, J=1.8, 1H), 5.24 (dd, J=10.2, J=4.4, 1H), 5.08 (dd, 1H, J=10.2, J=10.1, 1H), 4.57 (ddd, 1H, J=10.2, J=4.4, J=1.8, 1H), 4.29 (dd, 1H, J=12.5, J=4.0, 1H), 4.07 (dd, 1H, J=12.5, J=2.4, 1H), 4.05 (ddd, 1H, J=10.1, J=3.7, J=2.4, 1H), 3.72 (d, 1H, J=13.9, 1H), 3.28 (d, 1H, J=13.9, 1H), 2.48, 2.16, 2.15, 2.02, 1.98 (5 s, 3H each); $^{13}$C-NMR (100 MHz): δ 197.4, 170.7, 170.0, 169.2, 168.8, 168.1, 91.6 ($^1J_{C1-H1}$=177), 70.2, 69.2, 64.9, 61.5, 49.1, 32.9, 30.1, 20.8, 20.7, 20.6 (2C); MALDI-MS (m/z): [M+Na]⁺calcd for $C_{18}H_{25}NNaO_{11}S$, 486.1041; found, 486.1813; Analysis (calcd, found for $C_{18}H_{25}NO_{11}S$): C (46.65, 46.39), H (5.44, 5.46).

Compound No. 74 in Table A

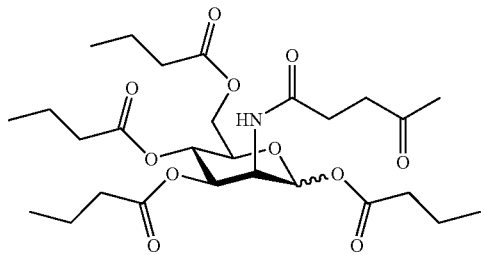

1,3,4,6-Tetra-O-butanoyl-2-(4-oxopentanamido)-2-deoxy-α,β-D-mannopyranose (But₄ManNLev)

To a stirred suspension of N-levulinoyl mannosamine (1.8 g, 6.5 mmol), prepared according to Mahal, L. K., Yarema, K. J., Bertozzi, C. R. *Science*, 276, 1125-1128 (1997), in pyridine (6.0 mL) at 22° C. was added butyric anhydride (6.0 mL, 37 mmol) followed by DMAP (cat.). After 24 h, the reaction mixture was co-concentrated with toluene (3×50 mL), the residue was dissolved in dichloromethane (100 mL) and washed successively with dilute HCl (~5%) (1×100 mL), water (1×100 mL) and saturated $NaHCO_3$ (1×100 mL). The organic layer was dried (anh. $Na_2SO_4$), filtered, and concentrated. Silica gel column chromatography of the residue gave pure But₄ManNLev (3.2 g, 85%) as a syrup.

Cell Culture Methods and Supplementation with Butyrate Derivatives 1-5

For cell culture studies, But₄ManNAc (1) (50) was used as a mixture of anomers (α/β=10/90), But₄GlcNAc (2) as pure α-anomer and But₅Man (3) as pure β-anomer (It is noteworthy that the intracellular hydrolysis of butyrate esters makes the anomeric configuration less relevant in these studies and we found similar cellular effects between the α- and β-anomers in long term toxicity). Stock solutions of the sugar analogs were made in ethanol at concentrations of 10 mM and 50 mM. In the case of cells growing in suspension the solutions of 1-4 (or an ethanol control at an equivalent volume) were coated onto dishes and the ethanol was allowed to evaporate prior to plating. Unless otherwise noted, throughout this study Jurkat cells (Clone E-6, ATCC, Manassas, Va.) were cultured in RPMI 1640 medium supplemented with 300 mg/L glutamine, 5.0% fetal bovine serum (HyClone, Logan, Utah) and 1.0% of a 100× dilution of a pen/strep stock solution containing penicillin (100 units/mL) and streptomycin (100 μg/mL); HL-60 cells (ATCC, Manassas, Va.) were cultured in RPMI 1640 medium supplemented with 10% FBS and pen/strep; and AD293 (HEK) cells (Stratagene, La Jolla, Calif.) were grown in DMEM medium with 10% FBS and pen/strep. In all cases, cells were incubated in a standard 37° C. in a 5.0% $CO_2$, water-saturated environment. Cell counting was performed with a Beckman-Coulter Z2 particle counter and hemacytometer.

Toxicity and Growth Inhibition Assays

Solutions of the analogs in EtOH (10 mM stock) were coated onto 24-well plates at a range of concentrations from 0-320 μM and ethanol was allowed to evaporate. Jurkat cells (1.0×10⁵ cells) in 0.5 mL of medium were plated in each well (day 0). On days 3 and 5, fresh medium (1.0 mL) was added to each well. Cell cultures were mixed by gentle pipetting and 100 μL of cell suspension was taken from each well and counted. On days 7, 9, 11, 13 and 15, 1.0 mL of cell suspension was removed from each well after thorough mixing and fresh medium (1.0 mL) was added. Cells were counted on day 15 and the cell density was plotted as a percentage of control (as was done for cell counts from days 3 and 5).

Cell Viability Assays

Jurkat cells (2.0×10⁵ cells/mL) were seeded with 1-4 at 200 μM in 6-well T. C. plates. Aliquots of cell suspension (20 μL) were removed on a daily basis diluted with either PBS (20 μL) or trypan blue solution (20 μL) and cell viability was determined by using the standard trypan blue exclusion method; three replicate counts were taken for each condition.

Morphological Changes to HEK293 and HeLa Cells

The studies on morphological changes induced by sodium butyrate (5) and But₄ManNAc (1) were performed following a reported procedure (45). Briefly, HeLa cells (200,000 cells per well in a 6-well plate) were plated and allowed to form monolayers. After 24 h, the supernatant was aspirated, fresh medium (4.0 mL) was added and treated with either ethanol (20 μL (0.5%), control), 5 (5.0 mM), or 1 (250 μM). For the AD 293 (HEK) cells 2.0×10⁶ cells in 10 mL of medium (100 mm tissue culture dishes) were plated and treated, immediately after plating, with either ethanol (50 μL, control), 5 (5.0 mM), or 1 (250 μM). Images were acquired at various time intervals under bright field using a Nikon Eclipse TE200 inverted microscope equipped with a DXM 1200 digital camera.

Luc-p21$^{WAF1/cip1}$ Luciferase Reporter Gene Assays

The plasmid Luc-p21$^{Cip1/WAF1}$ (a gift from Vogelstein Laboratory, JHMI, Baltimore, Md.) was amplified and purified utilizing a plasmid maxi kit (Cat. No. 12163. Qiagen, Valencia, Calif.) following the manufacturer's protocol. HEK cells ($2.5 \times 10^5$) were seeded in 3.0 mL medium and grown in 6-well T. C. plates. Transfection was performed using lipofectamine 2000 (Cat. No. 11668-019, Invitrogen, Carlsbad, Calif.) following the protocol supplier's protocol. Cells were trypsinized 24 h after transfection and seeded at 250,000 cells per well with concentrations of 1-4 shown in FIG. 3a or 1, 5, and ManNAc plus 5 at the concentrations shown in FIG. 3c. After 72 h, the cells were trypsinized, counted and lysed in 300 μL of luciferase cell culture lysis buffer and diluted five-fold in the same buffer. Luminometry was performed utilizing the 'Luciferase Assay System' (Cat. No. 1500, 4550, Promega, Madison, Wis.) following supplier's protocol. Luciferase Assay Reagent (100 μL) was added to the cell lysate (20 μL) in luminometer tubes (Cat. No. 55.476, Sarstedt, Newton, N.C.) and the luminescence was measured immediately using a Berthold Sirius Luminometer. The final values were normalized relative to ethanol-treated controls and reported on a per cell basis.

Endogenous $p21^{WAF1}$ Assays

Endogenous expression of $p21^{WAF1}$ was detected following a reported procedure (58) with minor modifications. Jurkat cells ($5.0 \times 10^6$ cells in 10 mL medium) were incubated with either ethanol or 1 (250 μM or 5 (2.5 mM). On a daily basis, aliquots of cells (~$1.0 \times 10^6$ per sample) were taken, washed with PBS ($2 \times 1.0$ mL), fixed with Reagent A (Fix and Perm Kit, Caltag Laboratories, CA, Cat. No. GAS-003) for 10 min at room temperature, washed with washing buffer (PBS containing 5.0% FBS, 0.1% $NaN_3$), re-suspended in 95% v/v methanol and kept on ice. After 30 min, cells were again washed with washing buffer and incubated with FITC-conjugated anti-$p21^{WAF1}$ antibody (Calbiochem, San Diego, Calif., Cat. No. OP64F) at 2.0 μg/mL in Reagent B (100 μL) (Fix and Perm Kit, Caltag Laboratories) for 1.0 h at room temperature in the dark. Finally, cells were re-suspended in washing buffer (500 μL) and analyzed by flow cytometry. Three replicate samples were taken for each condition and 10,000 events were counted for each sample.

Flow Cytometry Analysis of Cell Cycle Status

The cell cycle arrest induced by butyrate analogs was studied following the standard protocol (49). Briefly, Jurkat cells ($2.3 \times 10^5$ cells/mL) were incubated with various concentrations of 1 (0, 25, 50, 75, 100, 150 and 200 μM); 2 (200 μM); 3 (200 μM); and 4 (200 μM) for five days. The cells were then harvested, counted, washed twice with PBS, re-suspended in PBS (500 μL), added to a cold solution of 78% aqueous ethanol (4.5 mL) using a glass Pasteur pipette and kept at 2.0° C. for at least 24 h. The fixed cells were centrifuged twice to remove the ethanol completely, re-suspended in propidium iodide (PI)/ribonuclease A (RNase A) staining buffer (BD Pharmingen, Catalog No. 550825, San Diego, Calif.) (500 μL for $1.0 \times 10^6$ cells), incubated at 37° C. for 15 min and analyzed by flow cytometry. The cellular aggregates were excluded from single cell populations using an area-width plot (FL2—PT fluorescence) for the cell cycle status determination. At least 10,000 gated events were counted for each determination.

Time Course of Cell Cycle Status

Jurkat cells ($2.5 \times 10^5$ cells/mL) were incubated with either ethanol (0.2%) or 1 (100 μM or 200 μM). Aliquots of cell suspensions were taken on day 0 and days 2-6, washed with PBS (twice) and fixed in 75% ethanol at 2.0° C. for at least 48 h. The cells were stained with PI/RNase staining buffer and analyzed by flow cytometry as given above.

Assay for Total Sialic Acid Production

Jurkat cells ($5.0 \times 10^6$ cells in 10 mL medium) were incubated with 1-5 at various concentrations. After three days, the cells ($1.0 \times 10^6$ cells per sample) were lysed by freeze-thaw cycles (three times). The cell lysates were analyzed by using an adapted version of the periodate-resorcinol assay (36, 59) with the periodic acid oxidation step performed on ice to allow quantification of total (i.e., free monosaccharide plus glycoconjugate-bound) sialic acid. For each assay, a standard curve was obtained using N-acetylneuraminic acid (Pfanstiehl, Waukegan, Ill.) for calibration.

Toxicity of Sodium Butyrate (5) Towards Cells Primed with ManNAc

Jurkat cells ($5.0 \times 10^5$ per mL) were incubated with PBS and ManNAc at 50 or 100 mM. After 48 h, the cells were counted, harvested, washed once in fresh medium and plated in a 24-well plate containing various concentrations of sodium butyrate (5) (0-2.0 mM; a stock solution of 200 mM in PBS was used for dilutions and control samples). Cell cultures were maintained and growth was monitored for 15 days as described above under the toxicity and growth inhibition assays.

Experimental procedures essentially similar to those know in the art were examined and data on caspase-3 activity assay in Jurkat cells for dose dependent apoptosis induced by $But_4ManNAc$ (1) was collected. Such results are consistent with those expected by the compounds herein.

Butyrate Induced Cell Death is Dependent on the Core Sugar Moiety

To test the hypothesis that monosaccharides tune the activity of butyrate, perbutyrate derivatives of N-acetyl-D-mannosamine ($But_4ManNAc$, 1, FIG. 1B) and two control monosaccharides—N-acetyl-D-glucosamine ($But_4GlcNAc$, 2), and D-mannose ($But_5Man$, 3) were synthesized and tested on human cancer cells. To briefly explain the rationale for the control compounds, 2 is a C2 epimer of 1 that, if anything, should be protective via O-GlcNAc protein modification through an anti-stress mechanism (43) and 3 is the oxygen analog of 1 (i.e., it has an —OH group in place to the N-acetyl group at C2) but does not influence metabolic flux through the sialic acid biosynthetic pathway. Finally, tributyrin (4) and sodium butyrate (5) were included in certain experiments to serve as benchmarks for SCFA-based HDACi compounds that have already undergone clinical evaluation (19)).

Figure 2A:
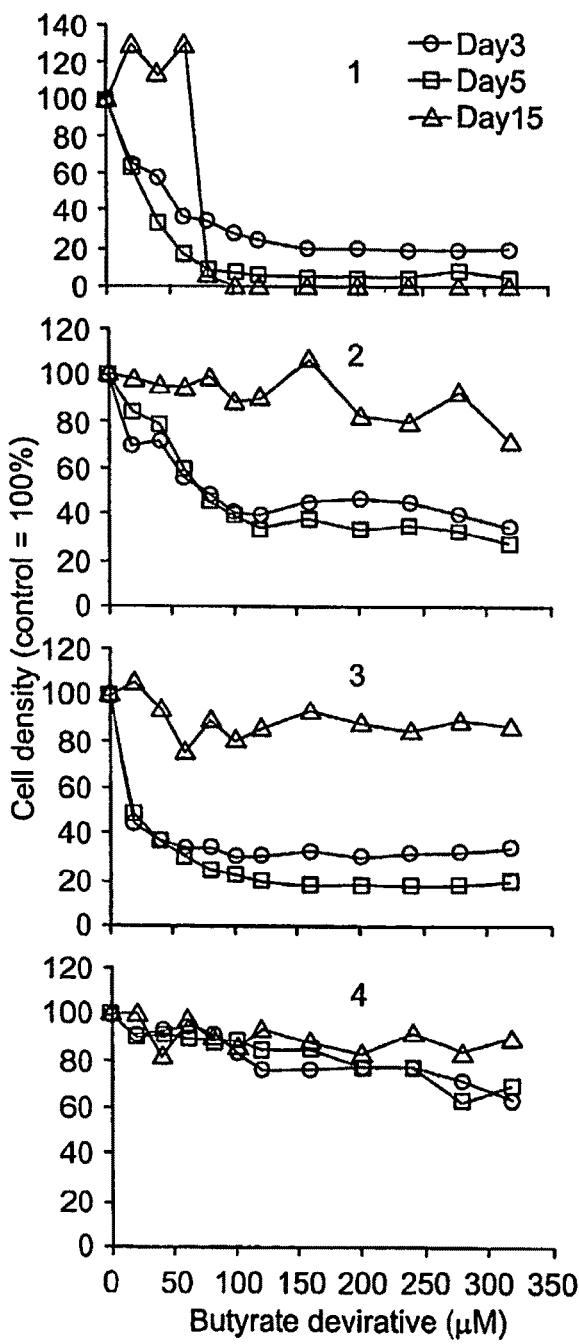
Figure 2B:
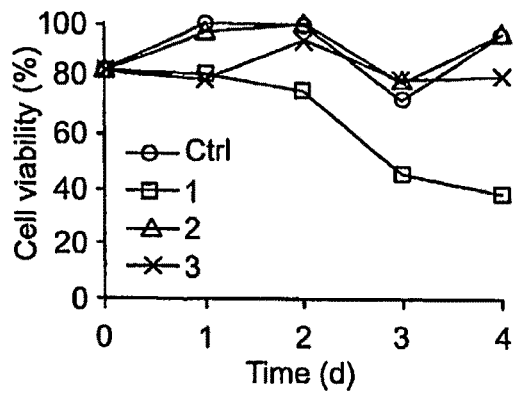
Figure 2C:
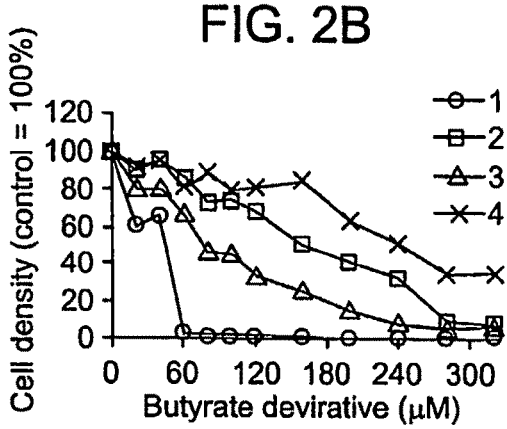

In initial assays, Jurkat (human T-lymphoma) cells were incubated with 1-4 and growth rates were monitored. As expected from the ability of butyrate to arrest cell cycle progression, 1-3 dramatically reduced cell proliferation at early time points (days 3 & 5) in a dose dependent manner (FIG. 2A). By contrast, 4 showed minimal inhibition up to the maximum concentration tested of 320 μM (FIG. 2A). Despite similar cell counts for 1-3 at days 3 and 5, trypan blue assays hinted that the underlying biological response to these compounds was different as 1, but not 2 or 3, exhibited reduced cell viability in this assay (FIG. 2B). Upon continued incubation, the early differences in cell viability became amplified and by day 15 cells treated with 2-4 resumed robust growth over the entire range of test concentrations (0-320 μM) whereas essentially all cells treated with 1 at concentrations ≥80 μM died. These results indicated that ManNAc, the core carbohydrate of 1, played a crucial role in preventing growth recovery and ensuring cell death. To test whether the synergistic effects between ManNAc and n-butyrate were general towards cancer cells, 1-4 were evaluated in several additional lines with similar results (representative data, for the HL-60 (neutrophil-derived) line, are given in FIG. 2C).

Figure 3A:
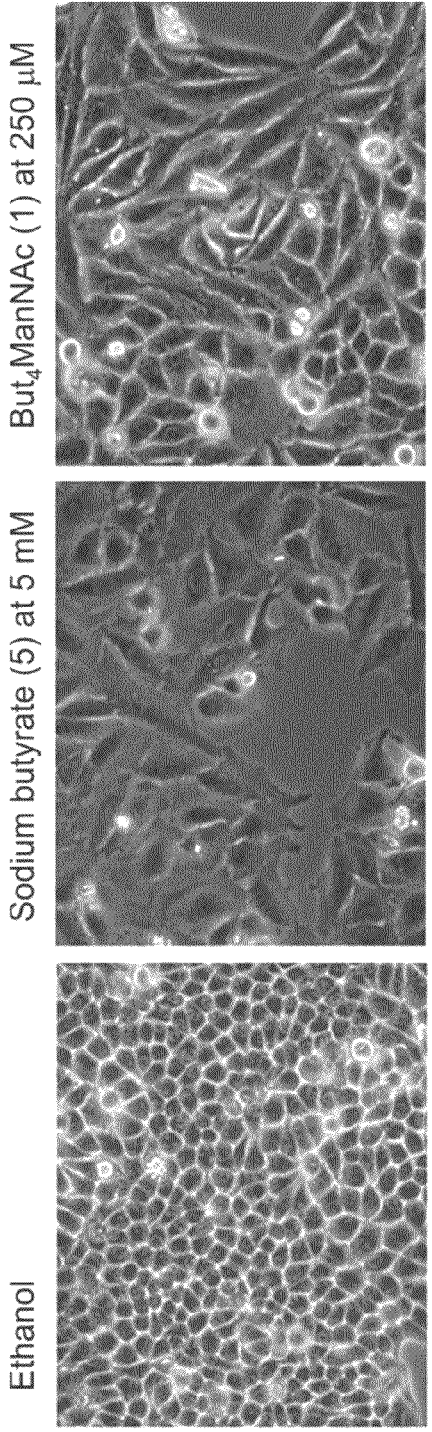
Figure 3B:
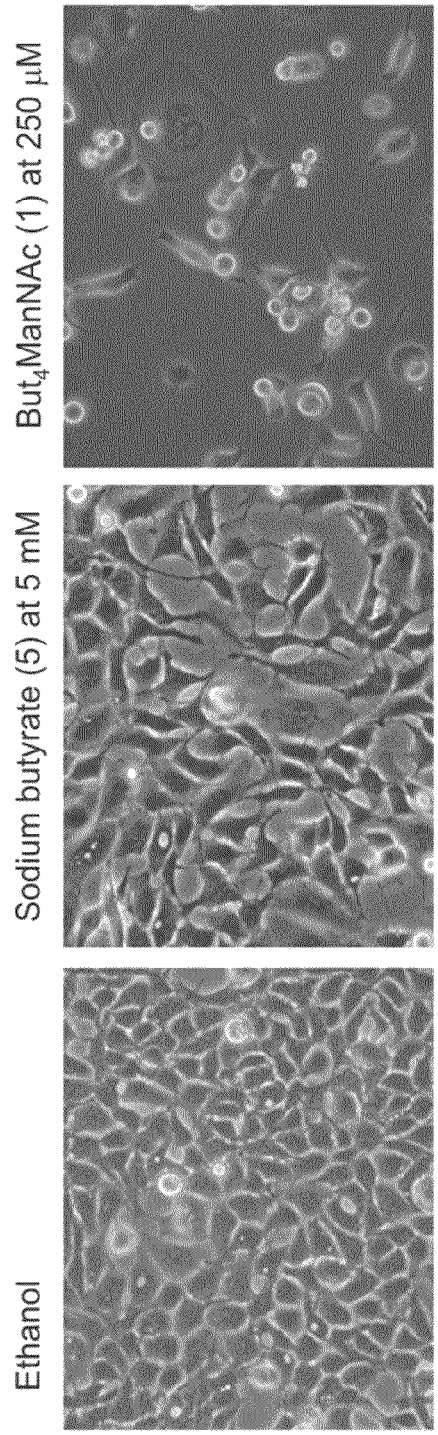

Next, based on seminal reports of the ability of butyrate to induce SCFA-characteristic differentiation of cancer cells (44), we tested the ability of 1 to induce similar morphological changes in HeLa cells (FIG. 3A). Upon three days of incubation, 1 induced differentiation of HeLa cells, similar to 5, as seen by increased spreading and long outgrowth of processes. A similar result was obtained for HEK AD293 cells with this line showed a greater degree of sensitivity to 1; it underwent a considerable degree of apoptosis under conditions (250 µM exposure for two days, FIG. 3B) that merely led to morphological changes in HeLa cells. Interestingly, in both cases cellular responses were experienced at much lower (~20×) concentrations for 1 than for sodium n-butyrate. Although much work remains—beyond the scope of this report—to uncover the detailed biological mechanism behind this response, it is intriguing to speculate that because butyrate increases the activity of sialyltransferases (45) responsible for production of gangliosides involved in apoptosis, (40, 41), these molecules are situated at the intersection of SCFA signaling and sialic acid metabolism and play a mechanistic role in the potent activity of 1. In this work, we focus on providing detailed experimental evidence that morphological changes supported by 1 (FIG. 3), as well as the ability of this compound but not 2-4 to "arrest and execute" cells (FIG. 2A), results from the butyrate groups functioning as HDACi (to provide growth arrest) while the ManNAc moiety simultaneously activates the sialic acid pathway (to induce apoptosis).

Hexosamine-Delivered Butyrate has Characteristic SCFA Activity

In this section, we present evidence for the first aspect of our model to describe the bioactivity of 1 against cancer cells—namely that sugar-delivered butyrate acts as an HDACi—by a set of three complementary assays. Specifically, activation of gene expression characteristic of HDACi, as exemplified by $p21^{WAF1}$-Up regulation, was demonstrated in a luciferase reporter assay, up regulation of endogenous levels $p21^{WAF1}$ was then tested upon exposure to 1 or sodium n-butyrate, and analysis of cell cycle progression through propidium iodide/ribonuclease A assays was done. Together, these assays provide convincing proof that sugar-delivery n-butyrate retains its characteristic SCFA bioactivity.

In the first assay done to verify that 1-4 supply butyrate to cells in an HDACi-active form, we evaluated luciferase activity from a luc-$p21^{WAF1/cip1}$ reporter plasmid (46) transiently transfected into HEK AD293 (human embryonic kidney) cells (47). When 1-4 were tested in this assay, which measures the up-regulation of gene expression driven by the cell cycle checkpoint protein $p21^{WAF1/Cip1}$ promoter—a hallmark of the butyrate response—luciferase expression increased in a dose dependent manner (FIG. 4A). To test whether $p21^{WAF1/cip1}$-promoter activation held across cell lines and for endogenous $p21^{WAF1}$, levels of this protein were evaluated in Jurkat cells treated with 1 and 5 and both compounds increased $p21^{WAF1}$ levels over a one week test period (FIG. 4B).

Of practical importance for future drug development efforts with SCFA-hexosamine hybrids, endogenous $p21^{WAF1/Cip1}$ gene activation was achieved at considerably (~10×) lower concentrations when cells were treated with 1 than with sodium n-butyrate (5, FIG. 4B). The gain in efficiency for 1 over 5 was even greater when these compounds were compared in the luc-$p21^{WAF1/Cip}$ reporter assay (FIG. 4C; note that the test concentrations were increased until a toxicity-associated decline in luc-$p21^{WAF1/cip1}$ levels occurred). A plausible explanation for the micromolar level efficiency of 1, compared to millimolar concentrations required for 5, was that the increased lipophilicity gained by masking the carboxylate groups of butyrate enhanced non-specific membrane diffusion. Moreover, the multivalent sugar scaffold allowed intracellular release of up to four equivalents of butyrate for each molecule entering the cell. Another—albeit unlikely—possibility was that ManNAc increased the efficiency of butyrate through a mechanism unrelated to its direct attachment of this SCFA via ester linkages, for example through up regulation a membrane transporter. In order to discount this possibility, we tested luc-$p21^{WAF1/Cip1}$ expression after incubating cells with a mixture of free monosaccharide form of ManNAc and 5 in a 1:4 ratio designed to mimic the relative molar ratios of the sugar and butyrate moieties in 1. The supplementation of 5 with ManNAc had no effect on luciferase activity (FIG. 4C) indicating that the micromolar-level efficiency achieved by 1 was contingent upon supplying the sugar and SCFA functionalities in the same molecule.

Figures 5A, 5B:
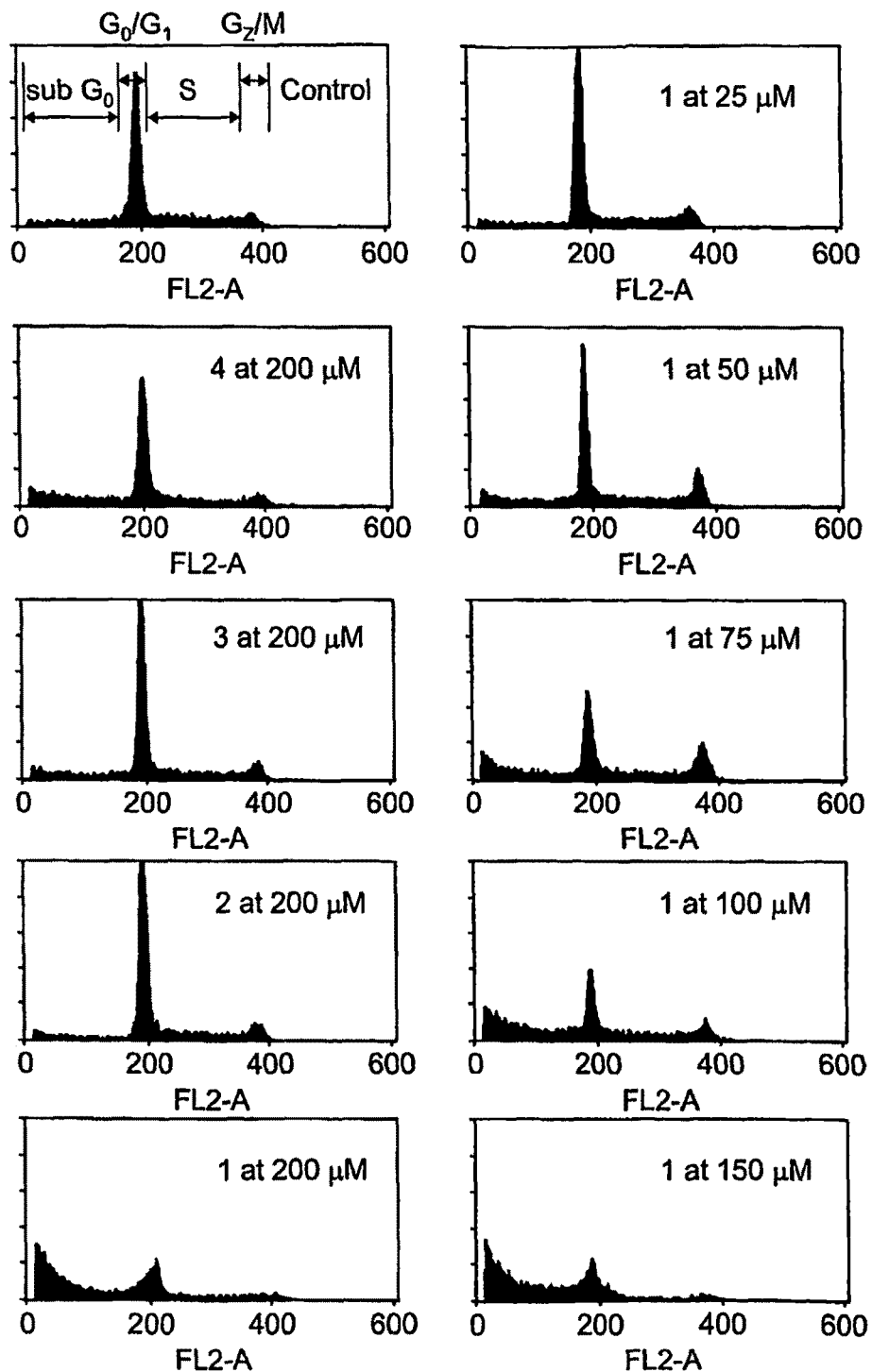

Having confirmed that 1-5 activated $p21^{WAF1/Cip1}$-driven gene expression consistent with the biological activity of SCFAs, we next tested whether 1-4 blocked cell cycle progression at the $G_2/M$ (4n) stage as n-butyrate does (48). Standard propidium iodide (PI)/ribonuclease A (RNase A) assays (49) in asynchronous Jurkat cells showed that cell accumulation at the $G_2/M$ stage occurred after incubation with 2-4 (5 days, 200 µM) without measurable apoptosis (FIG. 5A). In contrast, the majority of cells treated with 1 appeared to be apoptotic (<2n) with very few remaining at the $G_0/G_1$ (2n) stage. At lower concentrations (0-75 µM), however, 1 supported a stepwise decrease in $G_0/G_1$ accumulation with a concomitant increase in cells at the $G_2/M$ stage consistent with known ability of butyrate to arrest cell cycle progression (FIG. 5B). Non-viable cells (sub $G_0$) accumulated when concentrations of 1 exceeded 75 µM, a concentration consistent with the levels of this compound required for long term cell death (FIG. 2A).

A detailed comparison through PI/RNase A analysis of the kinetics of the accumulation of non-viable cells upon treatment with 1 (FIG. 6) confirms the growth inhibition and trypan blue toxicity data presented earlier (FIG. 2). Ethanol-treated Jurkat cells showed little change in cell cycle status up to day 4 (after which a minor increase in accumulation at the $G_0/G_1$ stage occurred due to growth saturation, i.e., proliferation of Jurkat cells slows dramatically upon reaching a density of $2-3 \times 10^6$ cells/mL). Upon treatment with 100 µM of 1 (FIG. 6B), there was strong cell cycle inhibition at the $G_2/M$ stage that was sustained until day 6 along with an increasing number of cells showing less than 2n (i.e., fragmented) DNA. At the higher dosage of 200 µM of 1 (FIG. 6C), cells accumulated more rapidly at the $G_2/M$ stage with a concomitant decrease in the $G_0/G_1$ stage. Significantly, by day 4 a substantial proportion of the cells showed DNA in the sub $G_0$ range, consistent with the loss of viability previously detected by trypan blue analysis (FIG. 2B); by day 6 this response was almost complete. Accumulation of signal in the sub $G_0$ range in PI/RNase A assays is consistent with the DNA fragmentation that occurs during apoptosis. Therefore, it was reasonable to conclude that the sub $G_0$ accumulation seen upon treatment with 1, combined with our previous extensive characterization of ManNAc analog-induced apoptosis in Jurkat cells (50, 51), indicated that this compound killed cells through an apoptotic mechanism. Nonetheless, to obtain direct evidence that the observed cell death induced by 1 occurred via apoptosis, we measured the caspase-3 activity (50) and found that it increased by ~4, 8, and 14-fold for Jurkat cells incubated with 25, 50, and 100 µM, respectively, of 1 for 48 h (see supplemental data).

Figure 7B:
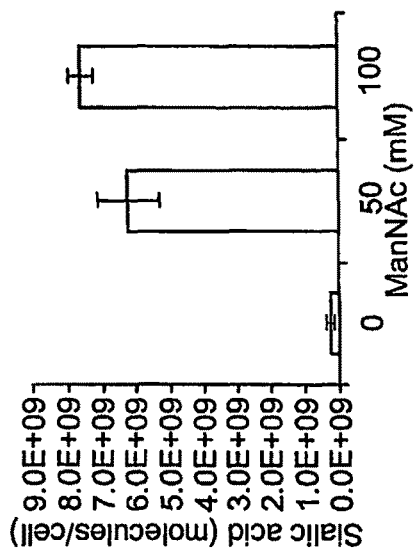
Figure 7A:
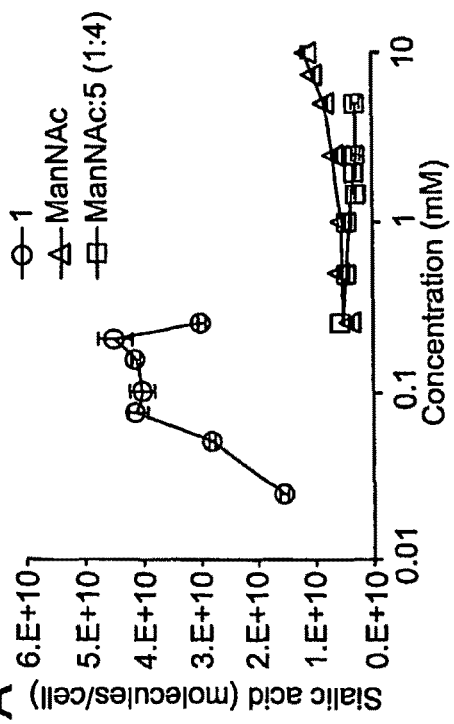
Figure 7D:
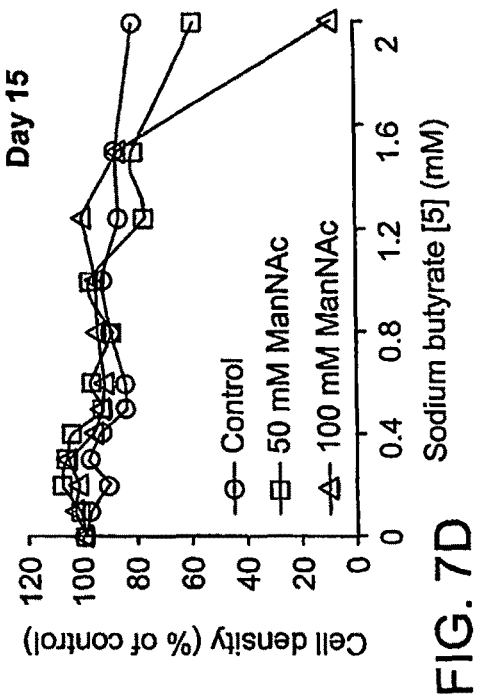

Increased Sialic Acid Biosynthesis Sensitizes Cells to Butyrate-Mediated Toxicity The hypothesis that 1 gains synergistic activity against cancer cells by combining the HDACi response elicited by butyrate, as described above, with glycosylation depends on the removal of butyrate from the core ManNAc moiety, presumably through hydrolytic release of n-butyrate from the carrier monosaccharide by non-specific esterases after cellular uptake (36, 50, 52, 53). Structural studies have established that the carboxyl group of butyrate must go "head first" into the binding pocket of histone deacetylases to achieve inhibition (12), which can only happen for sugar-delivered butyrate upon hydrolysis from the scaffold carbohydrate. Therefore, the efficient $p21^{WAF1}$ up regulation and cell cycle arrest reported above offers strong, but indirect, proof for hydrolysis of butyrate upon uptake by cells. Supplemental evidence for liberation of butyrate was provided by an increase in sialic acid biosynthesis (FIG. 7A) over the same concentration range where toxicity (FIG. 2) and $p21^{WAF1}$ up-regulation occurred (FIG. 4). A step by step consideration of the chemical reactions that occur during the biosynthesis of sialic acid (54, 55) indicate that a free hydroxyl group is required at the C1, C3, and C6 position of the ManNAc precursor. Consequently, the large increase in total sialic acid observed in cells incubated with 1 (FIG. 7A) was only possible upon removal of at least three of the four butyrate moieties of this hybrid molecule. It might be noted that the fate of the C4 butyrate ester of 1 remains ambiguous; based on the precedent established for acetyl esters, up to 50% of the esters at this position remain attached to the sugar throughout transit through the biosynthetic pathway and appear in glycoconjugate-bound sialic acids (56). Regardless of these minor unresolved details, 1 can clearly be regarded as a "pro-drug" that only attains full activity upon metabolic processing within a cell. The fact that ManNAc and butyrate had to be delivered together as a hybrid molecule to support efficient activation of sialic acid biosynthesis was firmly emphasized by showing that a mixture containing a 1:4 ratio of ManNAc and 5 did not increase sialic acid levels (FIG. 7A). In effect, from the perspective of sialic acid production, 1 is not only an efficient delivery vehicle for butyrate but is also beneficial for enhancing the transit of ManNAc across the plasma membrane.

Figure 7C:
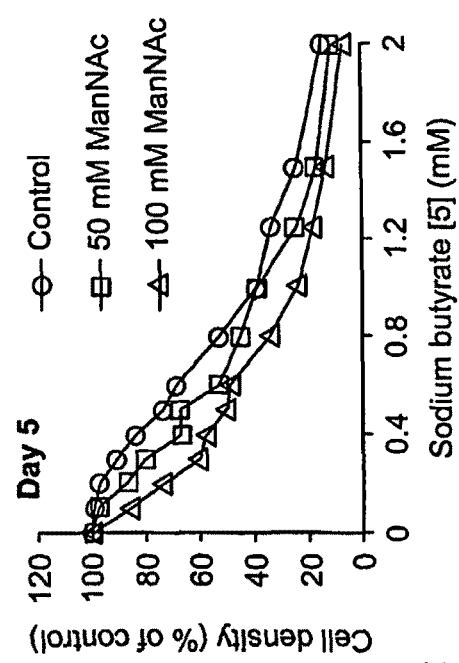

In our last set of experiments, we tested the ability of sialic acid to sensitize SCFA responses by priming cells with ManNAc. Based on our hypothesis that activation of sialic, acid biosynthesis has a synergistic effect with HDACi, ManNAc-primed cells were expected to show enhanced sensitivity to butyrate. Accordingly, Jurkat cells were first incubated with 0, 50 and 100 mM ManNAc for 48 h; ManNAc-treated cells showed a large increase (~20-30 fold) in total sialic acid (FIG. 7B). The test cells were then incubated with 5 and their growth was quantified at 5 and 15 days. At five days, the growth of ManNAc-treated cells was inhibited compared to untreated controls (FIG. 7C). By day 15, control cells had almost completely recovered from early inhibition but the ManNAc-treated cells showed susceptibility to sodium n-butyrate at 2.0 mM (FIG. 7D) and above (not shown). These results highlight two important features of the strategy exemplified by 1 of using sugar-SCFA hybrid molecules as anti-cancer agents. First, on a conceptual level, these results provide experimental support for the hypothesis that glycosylation pathways (shown by activation of sialic acid biosynthesis) can be exploited to augment the activity of existing drug candidates (in this case, the HDACi butyrate). Second, on a practical level, the levels of butyrate (2.0 mm) and ManNAc (100 mM) required for even partial cell inhibition and toxicity (FIG. 7D), when used separately, exceed realistic drug development parameters. When combined in the same molecule, however, the range for bioactivity (50-100 μM) compares favorably with other SCFA-based drug candidates (e.g., 4 (19) or synthetic molecules that include hydroxamates, cyclic peptides, aliphatic acids, and benzamides (4) already under clinical evaluation.

Additional examples of synthesis and characterization of analogs are known or are preformed essentially using methods described herein for:
$Prop_4ManNAc$, $Pent_4ManNAc$, $Hex_4ManNAc$, $Lau_4ManNAc$, $Pal_4ManNAc$, $St_4ManNAc$, $But_4ManNLev$, $Ac_5ManNTGc$ and $Ac_5ManNTPr$, $Ac_5ManNTBut$.

The primary significance of this research lies in the demonstration that the HDACi activity of butyrate can be augmented by design of the monosaccharide core structure that, in the past, had served only as an innocuous delivery vehicle. In particular, by using ManNAc to prime the sialic acid pathway, the coupling of this glycosylation pathway with SCFA-mediated cell cycle checkpoint control ensured not only that growth arrest, but ultimately the death, of cancer cells took place. Importantly, we showed that neither ManNAc nor butyrate, when supplied as separate molecules, could elicit a biological response at therapeutically relevant concentrations thereby emphasizing the need to combine both functionalities in a single hybrid molecule (i.e., a strategy of employing ManNAc as part of a therapeutic cocktail to augment SCFA activity would not be effective). In conclusion, Scheppach and Weiler recently published a review article where they compared the current flurry of butyrate-based anti-cancer research to putting "old wine in new bottles" (57); we believe that our approach to HDACi constitutes an important novel contribution to these efforts.

Loss of cell cycle checkpoint control and abnormal glycosylation are two major cellular aberrations associated with cancer. Defects in cell cycle checkpoints that arise from abnormal histone-chromatin interactions often can be corrected by natural short chain fatty acids (SCFA) such as butyrate or other histone deacetylase inhibitors (HDACi). In contrast to the multiple strategies now underway to develop HDACi for clinical use, glycosylation-targeted cancer therapies have been slow to emerge. To meet this void, we developed butyrate-hexosamine hybrids that target both protein production and carbohydrate expression and, by synergistic bioactivity, ensure both the "arrest" and "execution" of cancer cells. It is advantageously also potentially applicable as an alternative source of butyrate in a subject (e.g., animal, mammal, particularly one will a disease or disorder that makes fiber ingestion difficult) compared to fiber ingestion (which is upon ingestion broken down to provide butyrate in the colon and intestinal system). Narrowly, this work provides a promising approach to augment the anti-cancer potential of butyrate; broadly, it provides a concrete example of bringing glycosylation-based therapies closer to reality.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

A number of embodiments of the invention have been described. Nevertheless, it will be understood that various modifications may be made without departing from the spirit and scope of the invention. Accordingly, other embodiments are within the scope of the following claims.

REFERENCES

1. Møller M. B., (2003) Molecular control of the cell cycle in cancer: biological and clinical aspects. Dan. Med. Bull. 50, 118-138.
2. Dube D. H., Bertozzi C. R., (2005) Glycans in cancer and inflammation—potential for therapeutics and diagnostics. Nat. Rev. Drug Discov. 4, 477-488.
3. Fuster M. M., Esko J. D., (2005) The sweet and sour of cancer: glycans as novel therapeutic targets. Nat. Rev. Cancer 5, 526-542.
4. Kelly W. K., Marks P. A., (2005) Drug insight: histone deacetylase inhibitors—development of the new targeted anticancer agent suberoylanilide hydroxamic acid. Nat. Clin. Prac. Oncol. 2, 150-157.
5. Davie J. R., (2003) Inhibition of histone deacetylase activity by butyrate. J. Nut. 133, 2485S-2493S.
6. Dashwood R. H., Myzak M. C., Ho E., (2006) Dietary HDAC inhibitors: time to rethink weak ligands in cancer chemoprevention? Carcinogenesis 27, 344-349.
7. Drummond D. C., Noble C. O., Kirpotin D. B., Guo Z., Scott G. K., Benz C. C., (2005) Clinical development of histone deacetylase inhibitors as anticancer agents. Annu. Rev. Pharmacol. Toxicol. 45, 495-528.
8. Monneret C., (2005) Histone deacetylase inhibitors. Eur. J. Med. Chem. 40, 1-13.
9. Miller S. J., (2004) Cellular and physiological effects of short-chain fatty acids. Mini. Rev. Med. Chem. 4, 839-845.
10. Papeleu P., Vanhaecke T., Elaut G., Vinken M., Henkens T., Snykers S., Rogiers V., (2005) Differential effects of histone deacetylase inhibitors in tumor and normal cells-what is the toxicological relevance? Crit. Rev. Toxicol. 35, 363-378.
11. Novogrodsky A., Dvir A., Ravid A., Shkolnik T., Stenzel K. H., Rubin A. L., Zaizov R., (1983) Effect of polar organic compounds on leukemic cells. Butyrate-induced partial remission of acute myelogenous leukemia in a child. Cancer 51, 9-14.
12. Finnin M. S., Donigian J. R., Cohen A., Richon V. M., Rifkind R. A., Marks P. A., Breslow R., Pavletich N. P., (1999) Structures of a histone deacetylase homologue bound to the TSA and SAHA inhibitors. Nature 401, 188-193.
13. Rubenstein R. C., Zeitlin P. L., (1998) A pilot clinical trial of oral sodium 4-phenylbutyrate (Buphenyl) in deltaF508-homozygous cystic fibrosis patients: partial restoration of nasal epithelial CFTR function. Am. J. Respir. Crit. Car. Med. 157, 484-490.
14. Burlina A. B., Ogier H., Korall H., Trefz F. K., (2001) Long-term treatment with sodium phenylbutyrate in ornithine transcarbamylase-deficient patients. Mol. Genet. Metab. 72, 351-355.
15. Roomans G. M., (2003) Pharmacological approaches to correcting the ion transport defect in cystic fibrosis. Am. J. Respir. Med. 2, 413-431.
16. Kasumov T., Brunengraber L. L., Comte B., Puchowicz M. A., Jobbins K., Thomas K., David F., Kinman R., Wehrli S., Dahms W., Kerr D. A., Nissim I., Brunengraber H., (2004) New secondary metabolites of phenylbutyrate in humans and rats. Drug. Metab. Dispos. 32, 10-19.
17. Patnaik A., Rowinsky E. K., Villalona M. A., Hammond L. A., Britten C. D., Siu L. L., Goetz A., Felton S. A., Burton S., Valone F. H., Eckhardt S. G., (2002) A phase I study of pivaloyloxymethyl butyrate, a prodrug of the differentiating agent butyric acid, in patients with advanced solid malignancies. Clin. Cancer Res. 8, 2142-2148.
18. Reid T.; Valone F. H., Lipera W., Irwin D., Paroly W., Natale R., Sreedharan S., Keer H., Lum B., Scappaticci F., Bhatnagar A., (2004) Phase II trial of the histone deacetylase inhibitor pivaloyloxymethyl butyrate (Pivanex, AN-9) in advanced non-small cell lung cancer. Lung Cancer 45, 381-386.
19. Edelman M. J., Bauer K., Khanwani S., Tait N., Trepel J., Karp J., Nemieboka N., Chung E.-J., Van Echo D., (2003) Clinical and pharmacologic study of tributyrin: an oral brutyrate prodrug. Cancer Chemother. Pharmacol. 51, 439-444.
20. Pouillart P., Ronco G., Cerutti L, Trouvin J. H., Pieri F., Villa P., (1992) Pharmacokinetic studies of N-butyric acid mono- and polyesters derived from monosaccharides. J. Pharm. Sci. 81, 241-244.
21. Pouillart P., Douillet O., Scappini B., Gozzini A., Santini V., Grossi A., Pagliai G., Strippoli P., Rigacci L., Ronco G., Villa P., (1999) Regioselective synthesis and biological profiling of butyric and phenylalkylcarboxylic esters derivated from D-mannose and, xylitol: influence of alkyl chain length on acute toxicity. Eur. J. Pharm. Sci. 7, 93-106.
22. Corfield A. P., Myerscough N., Gough M., Brockhausen I., Schauer R., Paraskeva C., (1995) Glycosylation patterns of mucins in colonic disease. Biochem. Soc. Trans. 23, 840-845.
23. Sell S., (1990) Cancer-associated carbohydrates identified by monoclonal antibodies. Hum. Pathol. 21, 1003-1019.
24. Kobata A., Amano J., (2005) Altered glycosylation of proteins produced by malignant cells, and application for the diagnosis and immunotherapy of tumours. Immunol. Cell Biol. 83, 429-439.
25. Hadfield A. F., Mella S. L., Sartorelli A. C., (1983) N-acetyl-D-mannosamine analogues as potential inhibitors of sialic acid biosynthesis. J. Pharm. Sci. 72, 748-751.
26. Deshpande P. P., Danishefsky S. J., (1997) Total synthesis of the potential anticancer vaccine KH-1 adenocarcinoma antigen. Nature 387, 164-166.
27. Krug L. M., (2004) Vaccine therapy for small cell lung cancer. Semin. Oncol. 31, 112-116.
28. Hakomori S., (2001) Tumor-associated carbohydrate antigens defining tumor malignancy: basis for development of anti-cancer vaccines. Adv. Exp. Med. Biol. 491, 369-402.
29. Chen H., Wang Z., Sun. Z., Kim E. J., Yarema K. J. Mammalian glycosylation: An overview of carbohydrate biosynthesis. In: Yarema K. J., editor. Handbook of Carbohydrate Engineering. Boca Raton, Fla.: Francis & Taylor/CRC Press; 2005. p. 1-48.
30. Hanisch F. G., (2001) O-glycosylation of the mucin type. Biol Chem 382, 143-149.
31. Chou T. Y., Hart G. W., (2001) O-linked N-acetylglucosamine and cancer: messages from the glycosylation of c-Myc. Adv Exp Med Biol 491, 413-418.
32. Kim Y. S., Gum J., Brockhausen I., (1996) Mucin glycoproteins in neoplasia. Glycoconjug. J. 13, 693-707.
33. Hang H. C., Bertozzi C. R., (2005) The chemistry and biology of mucin-type O-linked glycosylation. Bioorg. Med. Chem. 13, 5021-5034.
34. Keppler O. T., Horstkorte R., Pawlita M., Schmidt C., Reutter W., (2001) Biochemical engineering of the N-acyl side chain of sialic acid: biological implications. Glycobiology 11, 11R-18R.

35. Goon S., Bertozzi C. R., (2002) Metabolic substrate engineering as a tool for glycobiology. J. Carbohydr. Chem. 21, 943-977.
36. Jones M. B., Teng H., Rhee J. K., Baskaran G., Lahar N., Yarema K. J., (2004) Characterization of the cellular uptake and metabolic conversion of acetylated N-acetylmannosamine (ManNAc) analogues to sialic acids. Biotechnol. Bioeng. 85, 394-405.
37. Ghosh P., Ender I., Hale E. A., (1998) Long-term ethanol consumption selectively inpairs ganglioside pathway in rat brain. Alcohol Clin. Exp. Res. 22, 1220-1226.
38. Suzuki O., Nozawa Y., Abe M., (2003) Sialic acids linked to glycoconjugates of Fas regulate the caspase-9-dependent and mitochondria-mediated pathway of Fas-induced apoptosis in Jurkat T cell lymphoma. Int, J. Oncol, 23, 769-774.
39. Eda S., Yamanaka M., Beppu M., (2004) Carbohydrate-mediated phagocytic recognition of early apoptotic cells undergoing transient capping of CD43 glycoprotein. J. Biol. Chem. 279, 5967-5974.
40. Malisan F., Testi R., (2002) GD3 in cellular ageing and apoptosis. Exp. Gerontol. 37, 1273-1282.
41. Chen H. Y., Varki A., (2002) O-acetylation of GD3: An enigmatic modification regulating apoptosis. J. Exp. Med. 196, 1529-1533.
42. Malykh Y. N., Schauer R., Shaw L., (2001) N-Glycolylneuraminic acid in human tumours. Biochimie 83, 623-634.
43. Zachara N. E., O'Donnell N., Cheung W. D., Mercer J. J., Marth J. D., Hart G. W., (2004) Dynamic O-GlcNAc modification of nucleocytoplasmic proteins in response to stress: A survival response of mammalian cells. J. Biol. Chem. 279, 30133-30142.
44. Fishman P. H., Brady R. O., (1976) Biosynthesis and function of gangliosides. Science 194, 906-915.
45. Fishman P. H., Simmons J. L., Brady R. O., Freese E., (1974) Induction of glycolipid biosynthesis by sodium butyrate in HeLa cells. Biochem. Biophys. Res. Commun. 59, 292-299.
46. El-Deiry W. S., Tokino T., Velculescu V. E., Levy D. B., Parsons R., Trent J. M., Lin D., Mercer W. E., Kinzler K. W., Vogelstein B., (1993) WAF1, a potential mediator of p53 tumor suppression. Cell 75, 817-825.
47. Bai L., Merchant J. L., (2000) Transcription factor ZBP-89 cooperates with histone acetyltransferase p300 during butyrate activation of p21(WAF1) transcription in human cells. J. Biol. Chem. 275, 30725-30733.
48. Blagosklonny M. V., Robey R., Sackett D. L., Du L., Traganos F., Darzynkiewicz Z., Fojo T., Bates S. E., (2002) Histone deacetylase inhibitors all induce p21 but differentially cause tubulin acetylation, mitotic arrest, and cytotoxicity. Mol. Cancer. Ther. 2002, 937-941.
49. Darzynkiewicz Z., Juan G., Bedner E. Determining cell cycle stages by flow cytometry. In: Bonifacino J. S., Dasso M., Harford J. B., editors. Current Protocols in Cell Biology. New York, N.Y.: John Wiley & Sons; 1999. p. 8.4.1-8.4.18.
50. Kim E. J., Sampathkumar S.-G., Jones M. B., Rhee J. K., Baskaran G., Yarema K. J., (2004) Characterization of the metabolic flux and apoptotic effects of O-hydroxyl- and N-acetylmannosamine (ManNAc) analogs in Jurkat (human T-lymphoma-derived) cells. J. Biol. Chem. 279, 18342-18352.
51. Kim E. J., Jones M. B., Rhee J. K., Sampathkumar S.-G., Yarema K. J., (2004) Establishment of N-acetylmannosamine (ManNAc) analogue-resistant cell lines as improved hosts for sialic acid engineering applications. Biotechnol. Prog. 20, 1674-1682.
52. Sarkar A. K., Fritz T. A., Taylor W. H., Esko J. D., (1995) Disaccharide uptake and priming in animal cells: inhibition of sialyl Lewis X by acetylated Gal b1,4GalcNAc b-Onaphthalenemethanol. Proc. Natl. Acad. Sci. U.S.A. 92, 3323-3327.
53. Højring N., Svensmark O., (1988) Molecular and catalytic properties of a butyrylesterase from human red cells and brain. Arch. Biochem. Biophys. 260, 351-358.
54. Tanner M. E., (2005) The enzymes of sialic acid biosynthesis. Bioorg. Chem. 33, 216-228.
55. Lawrence S. M., Huddleston K. A., Tomiya N., Nguyen N., Lee Y. C., Vann W. F., Coleman T. A., Betenbaugh M. J., (2001) Cloning and expression of human sialic acid pathway genes to generate CMP-sialic acids in insect cells. Glycoconjug. J. 18, 205-213.
56. Schwartz E. L., Hadfield A. F., Brown A. E., Sartorelli A. C., (1983) Modification of sialic acid metabolism of murine erythroleukemia cells by analogs of N-acetylmannosamine. Biochim. Biophys. Acta 762, 489-497.
57. Scheppach W., Weiler F., (2004) The butyrate story: old wine in new bottles? Curr. Opin. Clin. Nutr. Metab. Care 7, 563-567.
58. Siddiqui R. A., Jenski L. J., Harvey K. A., Wiesehan J. D., Stillwell W., Zaloga G. P., (2003) Cell-cycle arrest in Jurkat leukaemic cells: a possible role for docosahexaenoic acid. Biochem. J. 371, 621-629.
59. Jourdian G. W., Dean L., Roseman S., (1971) The sialic acids. XI. A periodate-resorcinol method for the quantitative estimation of free sialic acids and their glycosides. J. Biol. Chem. 246, 430-435.

What is claimed:

1. A compound of formula (I), or pharmaceutically acceptable salt, thereof:

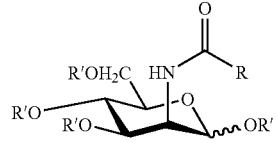

Formula (I)

wherein,
each R' is independently is —C(O)(CH$_2$)$_{2-7}$CH$_3$; and
R is selected from the group consisting of
CH$_2$(CH$_2$)$_{1-4}$COCH$_3$,
CH$_2$(CH$_2$)$_1$COCH$_2$CH$_3$,
CH$_2$N$_3$,
CH$_2$OCOCH$_3$,
(CH$_2$)$_{1-3}$SCOCH$_3$,
CH$_2$Ph,
CH(CH$_3$)$_2$,
CH$_2$CF$_3$,
(CH$_2$)$_3$CH(CH$_3$)$_2$, and
CH$_2$CH=CH(CH$_3$).

2. The compound of claim 1, wherein each R' is —C(O)(CH$_2$)$_n$CH$_3$ wherein n=2-4.

3. A pharmaceutical composition comprising a compound of Formula (I) in claim 1 and a pharmaceutically acceptable carrier.

4. The composition of claim 3, further comprising an additional therapeutic agent.

5. A kit comprising an effective amount of a compound of Formula (I) in claim 1 in unit dosage form, together with instructions for administering the compound to a subject suffering from or susceptible to a cancer disease or disorder or symptoms thereof.

6. A method of treating a subject suffering from or susceptible to a disease or disorder, the method comprising the step of administering to the subject a therapeutic amount of a compound of Formula (I) in claim 1 sufficient to treat the disease or disorder or symptoms thereof under conditions such that the disease or disorder is treated.

7. A method of treating a subject suffering from or susceptible to a disease or disorder, the method comprising the steps of: (i) identifying the patient as in need of administration of a histone deacetylase inhibitor (HDACi) compound that activates sialic acid biosynthesis; and (ii) administering to the subject a therapeutic amount of a compound of Formula (I) in claim 1 sufficient to treat the disease or disorder or symptoms thereof under conditions such that the disease or disorder is treated.

8. A method of inducing apoptosis in a subject, the method comprising the steps of identifying a subject as in need thereof and administering to the subject a therapeutic amount of a compound of the formula (I) in claim 1 capable of inducing apoptosis.

9. A method of inducing apoptosis in a subject, the method comprising the steps of identifying a subject as in need thereof and administering to the subject a therapeutic amount of a compound of the formula (I) in claim 1 capable of inducing apoptosis and activating sialic acid biosynthesis.

10. The method of claim 6, wherein the disease or disorder is not cancer.

11. A method of treating multiple sclerosis, Crohn's disease, rheumatoid arthritis, fibrosis, myocardial infarction, osteoid arthritis, Kaposi's sarcoma-associated herpes virus, Parkinson's disease, Huntington's disease, spinal muscular atrophy (increase survival motor neuron protein), cystic fibrosis, ulcerative colitis, antibiotic-associated diarrhea, stem cell fate and regenerative medicine, immune disorders, congenital abnormalities, infectious diseases and related diseases in a subject, the method comprising the steps of identifying a subject as in need thereof and administering to the subject a therapeutic amount of a compound of the of formula (I) in claim 1 sufficient to treat multiple sclerosis, Crohn's disease, rheumatoid arthritis, fibrosis, myocardial infarction, osteoid arthritis, Kaposi's sarcoma-associated herpes virus, Parkinson's disease, Huntington's disease, spinal muscular atrophy (increase survival motor neuron protein), cystic fibrosis, ulcerative colitis, antibiotic-associated diarrhea, stem cell fate and regenerative medicine, immune disorders, congenital abnormalities, infectious diseases and related diseases in a subject.

12. A method of sensitizing a cancer cell in a subject to anticancer agents, the method comprising the steps of identifying a subject as in need thereof and administering to the subject a therapeutic amount of a compound of formula (I) in claim 1 sufficient to sensitizing a cancer cell in a subject to anticancer agents.

13. A method of treating cancer in a subject, the method comprising the steps of administering to the subject a therapeutic amount of a compound of formula (I) in claim 1.

14. A method of modulating gene expression in a subject, the method comprising the steps of identifying a subject as in need thereof and administering to the subject a therapeutic amount of a compound of formula (I) in claim 1 sufficient to modulate the protein.

15. A method of modulating sialyltransferase activity in a subject, the method comprising the steps of identifying a subject as in need thereof and administering to the subject a therapeutic amount of a compound of formula (I) in claim 1 sufficient to modulate the sialyltransferase activity.

* * * * *